United States Patent
Callaghan et al.

(10) Patent No.: US 10,111,997 B2
(45) Date of Patent: Oct. 30, 2018

(54) APPARATUS AND METHODS FOR ACCESSING THE LYMPHATIC SYSTEM

(71) Applicants: Matthew J. Callaghan, Stanford, CA (US); Stephen A. Leeflang, Sunnyvale, CA (US); Christian S. Eversull, Palo Alto, CA (US)

(72) Inventors: Matthew J. Callaghan, Stanford, CA (US); Stephen A. Leeflang, Sunnyvale, CA (US); Christian S. Eversull, Palo Alto, CA (US)

( * ) Notice: Subject to any disclaimer, the term of this patent is extended or adjusted under 35 U.S.C. 154(b) by 720 days.

(21) Appl. No.: 14/160,547

(22) Filed: Jan. 21, 2014

(65) Prior Publication Data

US 2014/0243790 A1    Aug. 28, 2014

Related U.S. Application Data

(63) Continuation-in-part of application No. 13/887,277, filed on May 3, 2013, now Pat. No. 9,642,991, which
(Continued)

(51) Int. Cl.
*A61M 1/36* (2006.01)
*A61M 1/34* (2006.01)

(52) U.S. Cl.
CPC ........ *A61M 1/3653* (2013.01); *A61M 1/3496* (2013.01); *A61M 1/367* (2013.01);
(Continued)

(58) Field of Classification Search
CPC .............. A61M 1/3653; A61M 1/3609; A61M 1/3496; A61M 1/367; A61M 2202/0405;
(Continued)

(56) References Cited

U.S. PATENT DOCUMENTS 4,921,478 A * 5/1990 Solano ................ A61M 25/104
  604/103.07
4,957,484 A * 9/1990 Murtfeldt .......... A61M 25/0074
  604/102.02

(Continued)

OTHER PUBLICATIONS

Pflug, J. and J. Calnan, The Valves of the Thoracic Duct at the Angulus Venosus, Brit J. Surg, 1968, vol. 55, No. 12, December, 6 pages.
(Continued)

*Primary Examiner* — Bradley J Osinski
*Assistant Examiner* — Hamza Darb
(74) *Attorney, Agent, or Firm* — Vista IP Law Group LLP; William A. English

(57) ABSTRACT

Systems and methods are provided for performing a medical procedure within a patient's body that involves a thoracic duct including an ostium communicating with the patient's venous system. An apparatus is provided that includes a catheter including proximal and distal ends and a lumen extending therebetween. An expandable sealing member is carried beyond the distal end that is expandable from a delivery condition to a deployed condition in which the sealing member defines a concave contact surface shaped for engaging a vessel wall surrounding the outlet of the thoracic duct. The sealing member includes an aspiration port in the contact surface communicating with the catheter lumen for removing fluid from the thoracic duct.

20 Claims, 11 Drawing Sheets

Related U.S. Application Data is a continuation-in-part of application No. 13/100,297, filed on May 3, 2011, now Pat. No. 9,421,316.

(60) Provisional application No. 61/754,911, filed on Jan. 21, 2013, provisional application No. 61/642,180, filed on May 3, 2012.

(52) U.S. Cl.
CPC ... *A61M 1/3609* (2014.02); *A61M 2202/0405* (2013.01); *A61M 2205/3306* (2013.01); *A61M 2205/3317* (2013.01); *A61M 2230/207* (2013.01); *A61M 2230/208* (2013.01)

(58) Field of Classification Search
CPC .... A61M 2205/3306; A61M 2230/207; A61M 2230/208; A61M 2205/3317
See application file for complete search history.

(56) References Cited

U.S. PATENT DOCUMENTS

| | | | |
|---|---|---|---|
| 5,300,022 | A | 4/1994 | Klapper et al. |
| 5,391,143 | A | 2/1995 | Kensey |
| 5,766,151 | A | 6/1998 | Valley et al. |
| 6,443,925 | B1 | 9/2002 | Schaible et al. |
| 6,547,775 | B1 | 4/2003 | Blyakhman |
| 2003/0153943 | A1* | 8/2003 | Michael ............... A61F 2/013 606/200 |
| 2006/0100658 | A1 | 5/2006 | Obana et al. |
| 2007/0032754 | A1 | 2/2007 | Walsh |
| 2007/0282382 | A1 | 12/2007 | Shuros et al. |
| 2008/0004597 | A1 | 1/2008 | Lattouf et al. |
| 2008/0009719 | A1 | 1/2008 | Shuros et al. |
| 2008/0097412 | A1 | 4/2008 | Shuros et al. |
| 2008/0140000 | A1 | 6/2008 | Shuros et al. |
| 2009/0054805 | A1 | 2/2009 | Boyle |
| 2010/0217346 | A1 | 8/2010 | Shuros |
| 2011/0276023 | A1 | 11/2011 | Leeflang et al. |
| 2012/0029466 | A1 | 2/2012 | Callaghan et al. |
| 2012/0330132 | A1 | 12/2012 | Sorajja et al. |
| 2013/0245607 | A1 | 9/2013 | Eversull et al. |

OTHER PUBLICATIONS

The International Bureau of WIPO, International Preliminary Report on Patentability for corresponding International Application No. PCT/US2014/012408, Applicant: Matthew john Callaghan, May 1, 2014, 12 pages.

* cited by examiner

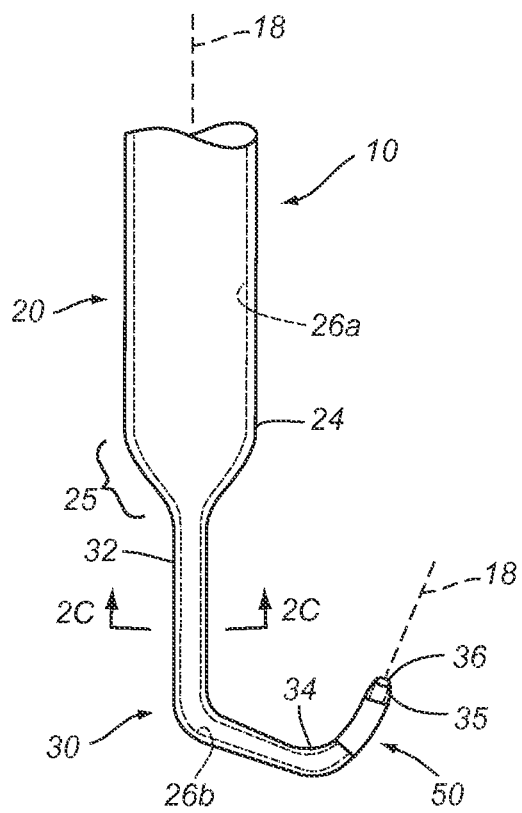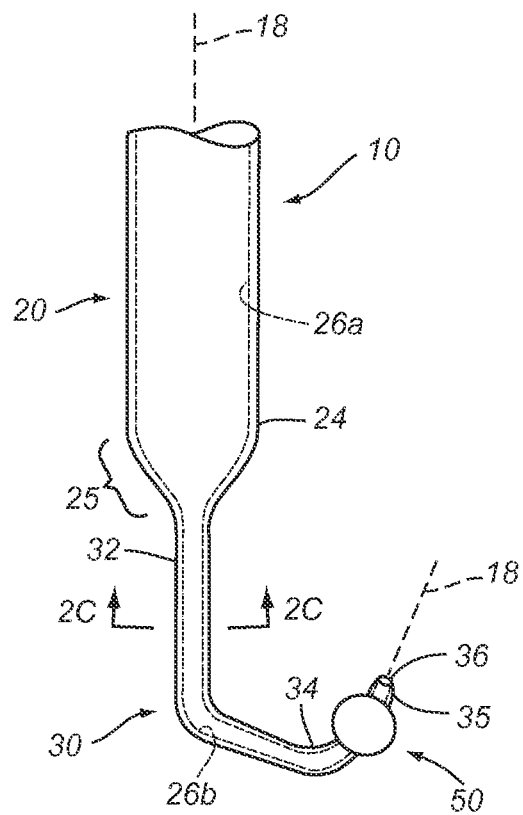
FIG. 2A
FIG. 2B
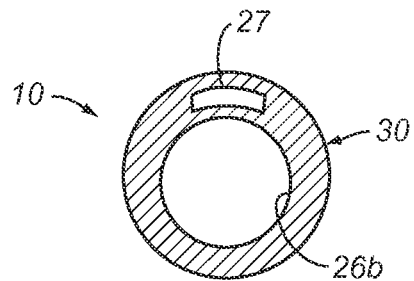
FIG. 2C

APPARATUS AND METHODS FOR ACCESSING THE LYMPHATIC SYSTEM

This application claims benefit of provisional application Ser. No. 61/754,911, filed Jan. 21, 2013, and is a continuation-in-part of co-pending application Ser. No. 13/887,277, filed May 3, 2013, which is a continuation-in-part of co-pending application Ser. No. 13/100,297, filed May 3, 2011, and also claims benefit of provisional application Ser. Nos. 61/642,180, filed May 3, 2012, the entire disclosures of which are expressly incorporated by reference herein.

FIELD OF THE INVENTION

The present invention relates generally to apparatus and methods used to perform medical procedures, and, more particularly, to devices, systems, and methods for accessing the lymphatic system of a patient, e.g., to remove, separate, and/or re-infuse lymphatic fluid and/or other components of lymph.

BACKGROUND

The lymphatic system includes a network of vessels generally separate from veins and arteries. Rather than whole blood, the lymphatic vessels carry lymphatic fluid (or lymph). The lymphatic system serves a variety of physiologic purposes, including returning interstitial fluid to the vascular space, transporting fats from the digestive tract, and transporting immune-mediating cells. The composition of lymphatic fluid is similar to plasma. It contains white blood cells, but generally does not contain red blood cells, platelets, or various other components of whole blood. The lymphatic system may be involved in a variety of pathologic states, including lymphatic obstruction leading to lymphedema, leakage of lymphatic fluid, which may lead to chylothorax, or the invasion and spread of malignant cells or particles such as exosomes which induce or lead leading to metastasis. The lymphatic system is involved in nearly any immune mediated response, whether to infectious agents (e.g., viruses, bacteria, parasites, etc.), malignancy, or in the setting of auto-immune disorders. The lymphatic system may serve as a repository for actively or latently infected cells in disorders such as HIV or may contain a higher concentration of malfunctioning cells in various immune system disorders. To achieve diagnosis and/or treatment of these and other conditions, it may be desirable to access the lymphatic system.

SUMMARY

The present invention is directed generally to apparatus, systems, and methods for performing medical procedures, and, more particularly, to apparatus, systems, and methods for accessing the lymphatic system of a patient, e.g., to remove, separate, and/or re-infuse lymphatic fluid.

Historically, the lymphatic vessels have been accessed rarely, generally by direct (e.g., surgical) approach. For example, some diagnostic procedures involve direct cannulation of peripheral lymphatic vessels, e.g., to infuse dye for identification of lymph nodes. Direct access of the central lymphatic vessels, such as the thoracic duct, is generally avoided. A defect, for example, in the thoracic duct generally does not readily close on its own, leading to significantly morbid conditions, such as chylothorax (persistent collection of lymphatic fluid around the lungs).

The lymphatic system does, however, eventually drain into the vasculature. A majority of lymphatic vessels come to a confluence in the thoracic duct which generally enters the venous system at the junction of the left subclavian vein and the left internal jugular vein in close proximity to the left vertebral vein. A single passive one-way valve marks the entrance to the thoracic duct from the venous circulation and serves to prevent reflux of whole blood into the duct when pressure in the venous system exceeds that in the terminal thoracic duct. This is a robust bi-leaflet valve composed partially of venous endothelium with an annulus generally between 2 and 4 mm wide. This terminal valve is widely conserved across patients, and is almost always present. Beyond this conserved anatomy the structure of the thoracic duct is less predictable, with multiple branches and confluences possible as it travels from the cervical neck into the thoracic cavity. A series of smaller valves made from more fragile lymphatic endothelium are located approximately every centimeter along the thoracic duct beyond the terminal valve. These valves generally facilitate one-way flow of lymphatic fluid into the venous system and also contribute as a secondary defense against the reflux of whole blood into the thoracic duct. Although not well studied, disruption of one or more of these valves may have negative consequences. Therefore, it may be desirable to protect valves and/or the lymphatic vessels themselves from damage.

Given the location of the thoracic duct, it may be feasible and desirable to access the lymphatic system by isolating or cannulating the thoracic duct via the venous system. Furthermore, given the risk of anatomic variation and increased fragility of the lymphatic endothelium beyond the terminal valve it may be desirable to access only the terminal portion of the duct, limiting instrumentation to the extent possible, (e.g. to the area adjacent the terminal and next thoracic duct valve). To minimize whole blood reflux when the terminal valve is held open during instrumentation, it may be desirable to create a seal at the terminal duct as well as the terminal valve itself in order to recreate the anti-reflux provision of the native terminal valve. Accessing the lymphatic vessels and removing and processing lymphatic fluid may be achieved using specialized catheter-based systems, as described elsewhere herein. Venous access may be achieved from any suitable location, including the left or right internal or external jugular, subclavian, axillary, anterior cubital, or femoral veins. Navigation to the thoracic duct may be aided by ultrasound, fluoroscopy, direct visualization, MRI, CT, and/or other imaging.

When accessing the lymphatic system trans-venously, it may be desirable to substantially isolate the thoracic duct or other lymphatic vessel, e.g., in order to selectively remove lymphatic fluid without removing significant amounts of whole blood, and/or to introduce fluids, agents, and the like selectively into the lymphatic vessels. It may also be desirable to selectively remove a portion of lymphatic fluid that is unneeded or pathologic and re-infuse the remaining portion back into the body.

Potential clinical applications may include drainage of lymphatic fluid for treatment of volume overload, for example, in the setting of congestive heart failure, depletion of lymphocytes or other immune system constituents, for example, in the setting of auto-immune disorders, preparation for transplantation procedures, treatment of infections residing primarily in immune-mediating cells, decompression of the lymphatic system to facilitate closure of leaking lymphatic vessels, treatment of lymphatic obstruction, and/or to otherwise remove fluid volume or pathologic constituents of lymphatic fluid. Further clinical applications may include diagnosis and/or monitoring of malignancy or metastatic spread of malignant cells or particles shed from primary tumors, or treatment of infection or malignancy, for example, by infusion of antibiotic, antiviral, antiparisitic, and/or chemotherapeutic agents directly into the lymphatic system. Other applications may include rapid immunization by direct introduction of antigens and/or antigenic material into the lymphatic system, sampling of nucleic acids and/or exosomes, or other applications where sampling or removal of lymphatic fluid or infusion of diagnostic or therapeutic agents is beneficial.

For example, the apparatus, systems, and methods herein may be used for treating volume overload, e.g., in congestive heart failure patients, by directly removing excess fluid from the body. When volume overload occurs in heart failure, excess fluid accumulates in the interstitial space to offload a failing heart. Patients become bloated and edematous due to peripheral fluid accumulation. In the lungs, where the interstitial space is limited, fluid may overflow into the airways and cause shortness of breath, which if left untreated can progress to respiratory arrest.

Volume overload is currently managed by two modalities: medications and dialysis. Medications to remove fluid from the body act by increasing kidney function and increasing urine output. Reversal of volume overload can take hours to days and is often incomplete. Dialysis mechanically filters fluid from blood in patients with poor kidney function. Dialysis is complex and expensive, requiring dedicated devices and highly trained staff. In the heart failure population, one third of all patients will also develop kidney disease. Given the significant drawbacks of both modalities, there is a crucial need to develop a more effective strategy for treating heart failure and other patients experiencing volume overload.

Instead of manipulating kidney function to increase urine output, the apparatus, systems, and methods herein may access the interstitial fluid compartment directly. The resulting treatments may be relatively rapid, safe, and/or cost effective compared to conventional treatments. Lymphatic drainage may provide an effective method for rapid fluid removal in volume overloaded patients. For example, any of the devices herein may be introduced through the central venous system to the thoracic duct ostium, e.g., using fluoroscopy, ultrasound, and/or direct visualization. A tip of the device may be sealed against the duct to draw fluid directly from the lymphatic system and into a vacuum container, e.g., located outside the body.

Such lymphatic drainage may safely and/or rapidly improve volume status and reverse symptoms of overload in heart failure patients. Additionally, in patients with cirrhosis or heart failure, lymphatic flow may significantly increase when drained to atmospheric pressure, with flow rates that may exceed twenty liters per day (20 L/day) or eight hundred thirty milliliters per hour (830 ml/hr), as compared to an average of one liter per day (1 L/day) in healthy subjects.

By comparison, the average rate of fluid removal in overloaded heart failure patients using conventional dialysis is less than eight hundred milliliters per hour (800 ml/hour). Urine output in similar patients given high doses of diuretic medications is generally less than three hundred milliliters per hour (300 ml/hr). This suggests the apparatus, methods, and systems herein may remove excess volume at a rate comparable to or faster than dialysis and significantly faster than medical treatment. Further, conventional treatments involve significant risks that may be avoided with the apparatus, systems, and methods herein. For example, medical diuersis may introduce risks of electrolyte imbalance, hypotension, and/or renal failure, while dialysis may introduce risks of hypotension and/or anticoagulation.

In addition, the apparatus and systems herein may be substantially atraumatic to the patient's venous system and may be navigated under ultrasound or fluoroscopy and/or direct visualization to the thoracic duct to isolate it from the venous circulation. In an exemplary embodiment, the apparatus may be configured to seal against the venous wall at the thoracic duct outlet and not engage or enter the thoracic duct itself. This may mitigate risks associated with entering and instrumenting the fragile lymphatic system. In alternative embodiments the thoracic duct may be cannulated to achieve a seal. For lymphatic drainage in CHF, atmospheric drainage (without active vacuum) may be sufficient to restore forward flow in the lymphatic system or an active source of vacuum may be included.

In accordance with an exemplary embodiment, In accordance with an exemplary embodiment, an apparatus is provided for accessing a thoracic duct of a patient's body that includes an outlet adjacent a confluence of an internal jugular vein and subclavian vein of the patient's body. The apparatus includes a tubular member including a proximal end, a distal end sized for introduction into a patient's vasculature, and an aspiration lumen extending between the proximal and distal ends. An expandable sealing member is provided on the distal end that is expandable from a delivery condition sized for introduction into a patient's vasculature to a deployed condition in which the sealing member defines a concave contact surface shaped for engaging a vessel wall surrounding the outlet of the thoracic duct. The sealing member may include an aspiration port in the contact surface communicating with the aspiration lumen for removing fluid from the thoracic duct through the aspiration port into the aspiration lumen.

In accordance with another embodiment, an apparatus is provided for accessing a thoracic duct of a patient's body that includes an outlet adjacent a confluence of an internal jugular vein and subclavian vein of the patient's body that includes a tubular member including a proximal end, a distal end, and an aspiration lumen extending between the proximal and distal ends, a frame carried on the distal end, and a flexible sealing member carried by the frame. The frame includes first and second arms including first fixed ends coupled to the distal end of the tubular member and second free ends, the free ends movable away from one another to an expanded configuration in which the arms define a generally "V" shape and movable towards one another to a collapsed configuration. The sealing member may include opposite ends attached to the arms such that the sealing member defines an outer contact surface, the sealing member movable between a delivery condition when the arms are in the collapsed configuration for introduction into a patient's vasculature and a deployed condition when the arms are in the expandable configuration in which the outer contact surface is shaped for engaging a vessel wall surrounding the outlet of the thoracic duct, the sealing member comprising an aspiration port in the outer contact surface communicating with the aspiration lumen for removing fluid from the thoracic duct through the aspiration port into the aspiration lumen.

In accordance with still another embodiment, a method is provided for accessing a thoracic duct of a patient's body that includes introducing a distal end of a tubular member into a patient's vasculature with a sealing member extending distally from the distal end in a delivery condition. The tubular member may be advanced until the distal end is disposed adjacent a junction of the patient's left internal jugular vein and the patient's left subclavian vein. The sealing member may deployed adjacent the junction such that a frame of the sealing member expands to define a generally "V" shape and a resilient member of the sealing member is expanded by the frame to define a concave outer contact surface oriented away from the tubular member distal end. The tubular member may be manipulated to press the contact surface against a vessel wall surrounding an outlet of the thoracic duct and substantially isolate the thoracic duct from the left internal jugular vein and left subclavian vein, whereupon fluid may be removed from the thoracic duct through an aspiration port in the contact surface communicating with an aspiration lumen within the tubular member.

In accordance with yet another embodiment, an apparatus is provided for accessing a thoracic duct of a patient's body that includes an outlet adjacent a confluence of an internal jugular vein and subclavian vein of the patient's body that includes a tubular member including a proximal end, a distal end sized for introduction into a patient's vasculature, and an aspiration lumen extending between the proximal and distal ends. A frame extends distally from the distal end including a pair of spaced apart struts including distal ends coupled together to provide a substantially atraumatic distal tip for the frame, the struts biased to a generally "J" shape and elastically movable to a substantially straight configuration. A flexible sealing member including opposite longitudinal edges may be attached to the struts such that the sealing member extends between the struts and defines a concave outer contact surface when the struts are in the "J" shape, the sealing member comprising an aspiration port in the contact surface, and a flexible tubular extension may extend between the sealing member and the tubular member distal end, and including a fluid path communicating between the aspiration port in the contact surface and the aspiration lumen for removing fluid from the thoracic duct through the aspiration port into the aspiration lumen.

In accordance with yet another embodiment, an apparatus is provided for accessing a thoracic duct of a patient's body that includes an outlet adjacent a confluence of an internal jugular vein and subclavian vein of the patient's body that includes a tubular member comprising a proximal end, a distal end sized for introduction into a patient's vasculature, and an aspiration lumen extending between the proximal and distal ends. A frame support may extend distally from the distal end and biased to a generally "J" shape and elastically movable to a substantially straight configuration, the frame support terminating in a frame support tip, and a flexible sealing member may be carried on the frame support tip and expandable from a delivery condition to a deployed condition to define a concave contact surface, the sealing member comprising an aspiration port in the contact surface. A flexible tubular extension may extend between the sealing member and the tubular member distal end, and including a fluid path communicating between the aspiration port in the contact surface and the aspiration lumen for removing fluid from the thoracic duct through the aspiration port into the aspiration lumen.

In accordance with an exemplary embodiment, an apparatus is provided for accessing a thoracic duct of a patient's body that includes a tubular member comprising a flexible, substantially straight proximal portion and a flexible, curved distal portion, wherein the proximal portion has a first length and a first outer diameter, and the distal portion has a second length and a second outer diameter, the second length shorter than the first length and the second outer diameter is smaller than the first outer diameter; and a balloon on the distal portion adjacent a distal tip thereof, the balloon sized for substantially isolating the thoracic duct when expanded therein.

In accordance with still another embodiment, an apparatus is provided for accessing a thoracic duct of a patient's body that includes a tubular member comprising a flexible, substantially straight proximal portion sized for introduction into a vein and a flexible, curved distal portion sized for introduction into a thoracic duct, and an aspiration lumen extending from a proximal end of the proximal portion to one or more inlet ports on a distal tip of the distal portion; and an expandable member on the distal portion adjacent the distal tip, the expandable member expandable from a collapsed configuration to allow introduction into a thoracic duct and an expandable configuration for substantially isolating the thoracic duct when expanded therein. In addition, the distal portion and the proximal portion may have one or more of the following: a) wherein the proximal portion has a first length and the distal portion has a second length, the second length shorter than the first length; b) wherein the proximal portion has a first outer diameter, and the distal portion has a second outer diameter, the second outer diameter is smaller than the first outer diameter; c) wherein the distal portion has greater flexibility than the proximal portion; d) wherein the distal portion is formed from softer materials than the proximal portion; and e) wherein the aspiration lumen has a first inner cross-section in the proximal portion and a second inner cross-section in the distal portion, the second cross-section smaller than the first inner cross-section.

In accordance with yet another embodiment, a method is provided for accessing a thoracic duct of a patient's body that includes providing a tubular member comprising a proximal portion and a flexible distal portion having a curvilinear shape in a relaxed state and terminating in a distal tip, the distal portion having a smaller outer diameter than the proximal portion; introducing the tubular member into a patient's vasculature via a percutaneous access site in the patient's left internal jugular vein; advancing the tubular member until the distal portion is disposed within a junction of the left internal jugular vein and the patient's left subclavian vein and the proximal portion is disposed through the access site and in the left internal jugular vein; manipulating the tubular member to orient the distal tip towards the thoracic duct; retracting the tubular member to direct the distal tip into the thoracic duct beyond a terminal valve of the thoracic duct; and expanding an expandable member on the distal portion adjacent the distal tip within the thoracic duct beyond the terminal valve to substantially isolate the thoracic duct from the left internal jugular vein and left subclavian vein.

In accordance with still another embodiment, a method is provided for accessing a thoracic duct of a patient's body that includes providing a tubular member comprising a proximal portion and a flexible distal portion having a curvilinear shape in a relaxed state and terminating in a distal tip, the distal portion having a smaller outer diameter than the proximal portion; introducing the tubular member into a patient's vasculature; advancing the tubular member until the distal portion is disposed within a junction of the left internal jugular vein and the patient's left subclavian vein; manipulating the tubular member to orient the distal tip towards the thoracic duct; retracting the tubular member to direct the distal tip into the thoracic duct beyond a terminal valve of the thoracic duct; and expanding an expandable member on the distal portion adjacent the distal tip within the thoracic duct beyond the terminal valve to substantially isolate the thoracic duct from the left internal jugular vein and left subclavian vein.

In accordance with another embodiment, a method is provided for performing a medical procedure within a patient's body, the body comprising a thoracic duct including an ostium communicating with the patient's venous system that includes introducing a distal portion of a tubular member through the patient's venous system into a body lumen adjacent the ostium of the thoracic duct, the distal portion biased to a curvilinear configuration; manipulating the tubular member until a distal tip of the distal portion enters the ostium of the thoracic duct; retracting the tubular member to direct the distal portion into the thoracic duct until an expandable member on the distal portion passes through a terminal valve of the thoracic duct; expanding the expandable member within the thoracic duct beyond the terminal valve to substantially isolate the thoracic duct from the body lumen; and performing a medical procedure via the thoracic duct.

In accordance with yet another embodiment, a system is provided for performing a medical procedure via a thoracic duct of a patient's body that includes a catheter or other tubular member including a proximal end, a distal end sized for introduction into a body lumen, and an aspiration lumen extending from the proximal end to a port in the distal end. An expandable member may be provided on the distal end, e.g., sized and/or shaped for substantially isolating the thoracic duct when expanded within the body lumen or thoracic duct itself. One or more external components may be coupled to the proximal end of the tubular member, e.g., a source of vacuum for removing fluid within the body lumen via the port and aspiration lumen, a detector for analyzing the fluid removed from the body lumen to identify lymphatic fluid, a separator for separating the lymphatic fluid or components of the lymphatic fluid from other fluid in the fluid removed from the body lumen, and/or a container for collecting the lymphatic fluid or components of the lymphatic fluid separated from other fluid.

In accordance with another embodiment, a method is provided for performing a medical procedure within a patient's body that includes a thoracic duct including an ostium communicating with the patient's venous system. A distal end of a tubular member may be introduced through the patient's venous system into a body lumen adjacent the ostium of the thoracic duct. An expandable member on the distal end of the tubular may be expanded adjacent the ostium, e.g., within the body lumen or the thoracic duct itself, and used to substantially isolate the thoracic duct from the body lumen, whereupon a medical procedure may be performed via the thoracic duct. For example, lymphatic fluid may be removed from the thoracic duct through a lumen of the tubular member and/or one or more agents may be introduced into the thoracic duct through the tubular member.

In an exemplary embodiment, fluid may be removed from the patient's body through a lumen of the tubular member, and the removed fluid may be analyzed to determine whether the fluid comprises lymphatic fluid or blood. For example, if the fluid comprises blood, the thoracic duct may not be isolated from the body lumen, and the removal of fluid may be stopped and/or the fluid may be directed to a waste container. If the fluid is lymphatic fluid, the fluid may be directed to a storage container, or components of the lymphatic fluid may be separated from other components of the fluid, and the separated components may be directed to a storage container. Optionally, the stored lymphatic fluid or the separated components of the lymphatic fluid may be infused back into the patient's body, if desired.

Other aspects and features of the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments of the invention, in which:

FIGS. 2A and 2B are details of a distal portion of the apparatus of FIG. 1, showing a balloon on the distal portion in collapsed and enlarged configurations, respectively.

FIG. 2C is a cross-section of the distal portion of the apparatus of FIGS. 2A-2B taken along line 2C-2C.

10A and 10B including a balloon that may expanded to enhance engagement of the sealing member around the outlet of the thoracic duct.

Figure 13A:
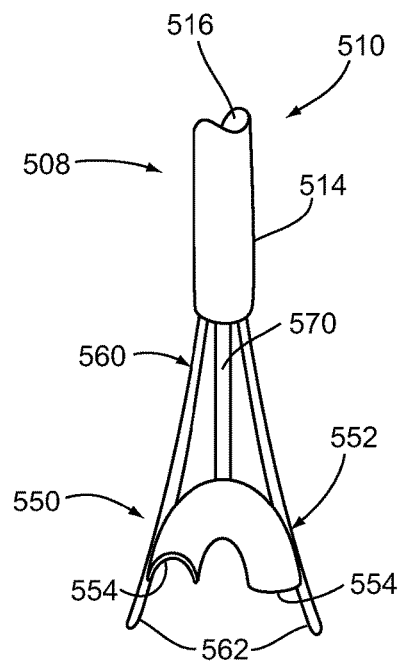
Figure 13B:
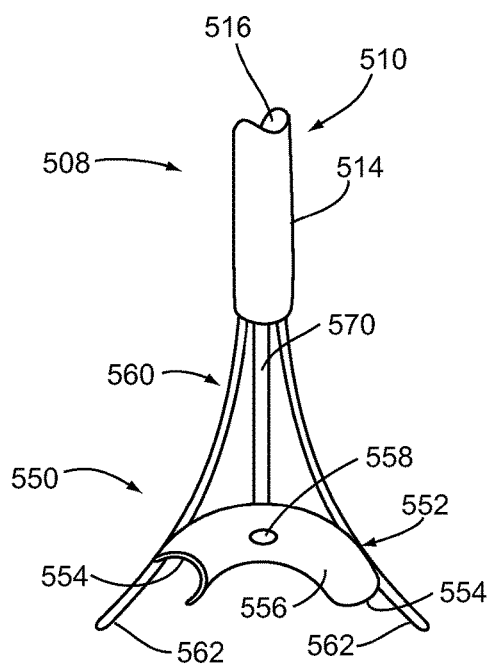

FIGS. 13A and 13B are side views of a distal portion of another embodiment of a catheter including a sealing member formed from a silicone body.

Figure 14:
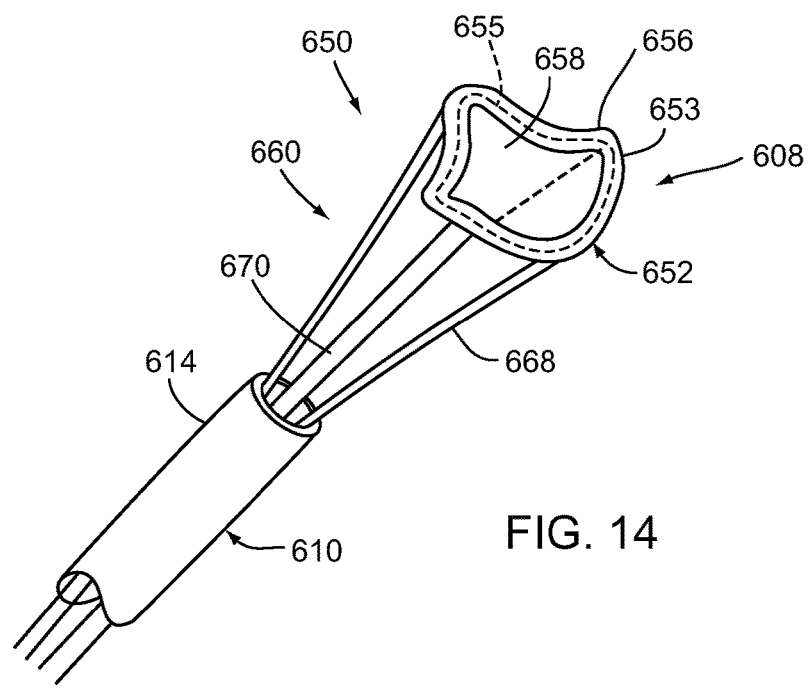

FIG. 14 is a perspective view of a distal portion of yet another embodiment of a catheter including a sealing member carried by a frame including actuatable struts for adjusted the shape of the sealing member to enhance engagement of the sealing member around the outlet of the thoracic duct.

Figure 15A:
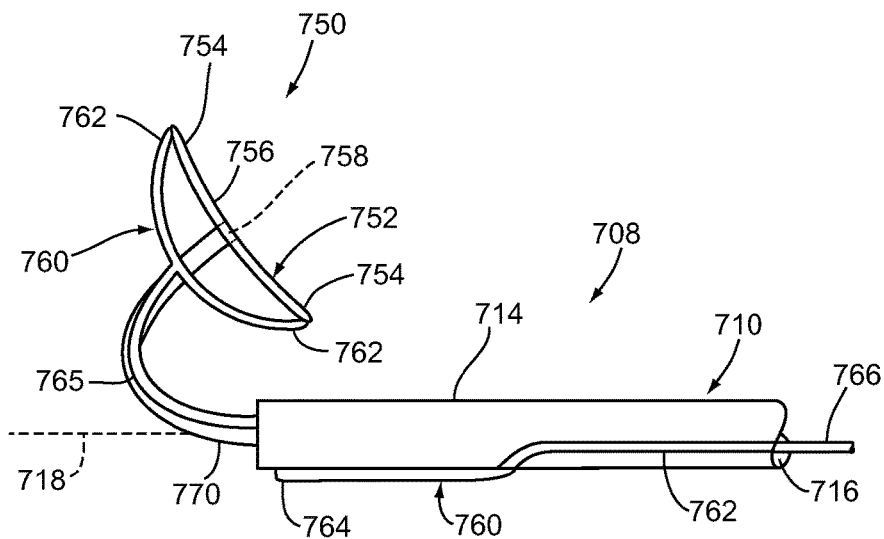

FIG. 15A is a side view of a distal portion of still another embodiment of a catheter including a pre-shaped frame carrying a sealing member and an expandable stabilizing member.

Figure 15B:
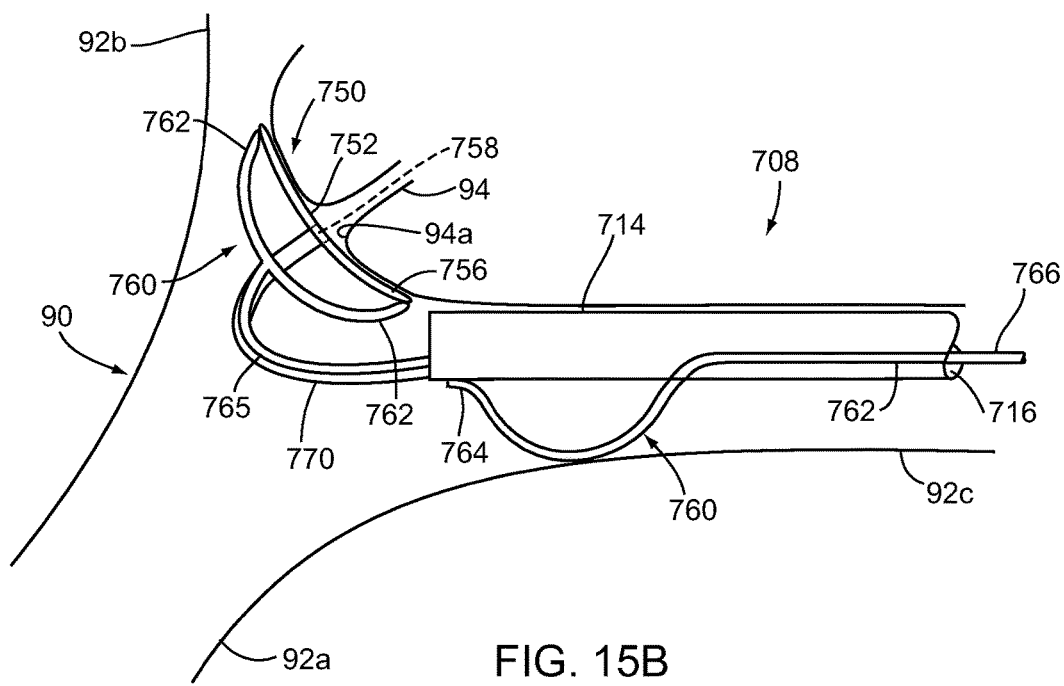

FIG. 15B is a detail of a patient's body, showing the distal portion of the catheter of FIG. 15A positioned within the confluence of the internal jugular and subclavian veins and the stabilizing member deployed to enhance engagement of the sealing member around the outlet of the thoracic duct.

Figure 16:
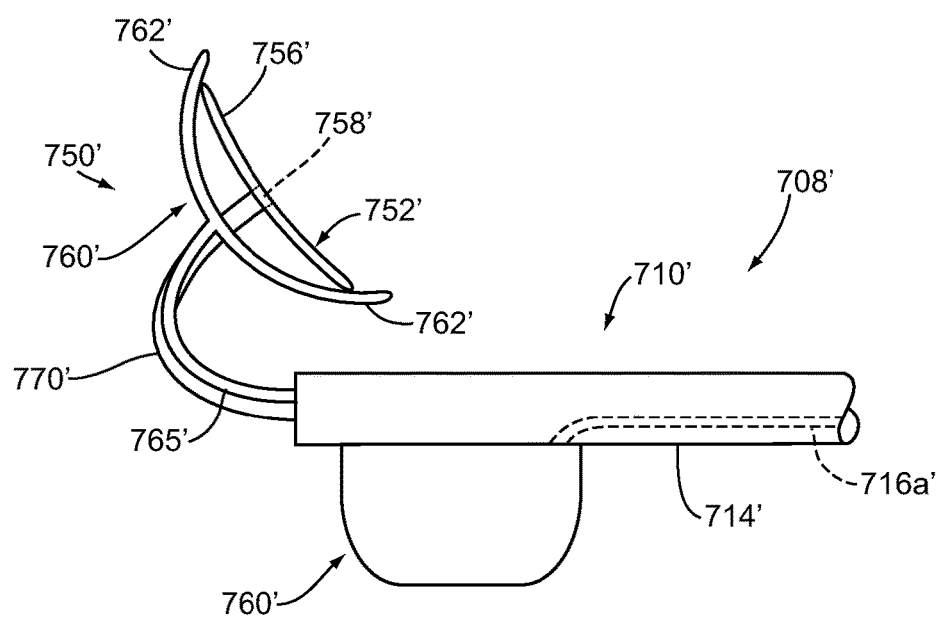

FIG. 16 is a detail of a patient's body, showing a distal portion of yet another embodiment of a catheter including a pre-shaped frame carrying a sealing member and an alternative expandable stabilizing member deployed to enhance engagement of the sealing member around the outlet of the thoracic duct.

DETAILED DESCRIPTION OF THE EXEMPLARY EMBODIMENTS

Figure 1:
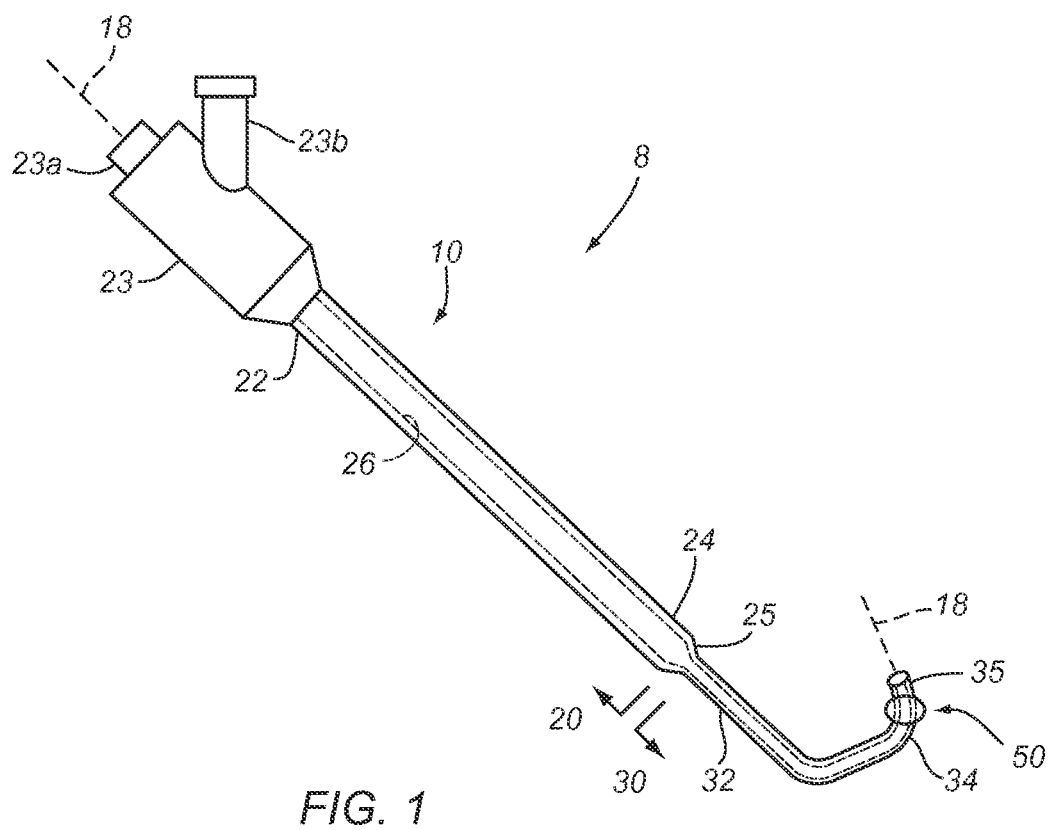
FIG. 1 is a perspective view of an exemplary embodiment of an apparatus for accessing a thoracic duct.

Turning to the drawings, FIGS. 1-2B show an exemplary embodiment of an apparatus 8 for accessing and/or isolating the lymphatic system of a patient 90 (not shown, see, e.g., FIG. 5 for anatomical references), e.g., to aspirate or otherwise draw lymphatic fluid from the thoracic duct 94, as described further below. Generally, the apparatus 8 includes a catheter or other tubular member 10 including a proximal or main portion 20, e.g., sized and/or shaped for introduction into a blood vessel of the patient, such as a jugular vein 92b (not shown, see FIG. 5), and a relatively smaller distal portion 30, e.g., sized and/or shaped for introduction into a thoracic duct 94 of the patient 90 (also not shown, see FIG. 5), thereby defining a central longitudinal axis 18 for the apparatus 8.

A balloon or other expandable member 50 may be provided on the distal portion 30, e.g., sized for introduction into a thoracic duct in a collapsed configuration and expandable to an enlarged configuration for substantially sealing and/or isolating the thoracic duct 94, as described further below. The balloon 50 may be formed from elastic material, e.g., such that the balloon 50 may be inflated to multiple diameters to accommodate engaging the wall of thoracic ducts of various sizes and/or shapes, to provide a substantially fluid-tight seal without applying excessive forces against the wall. The balloon 50 may be sufficiently compliant such that inflation within the annulus of the terminal valve of the thoracic duct will deform and seal the balloon against the annulus without stretching or damaging the annulus itself.

Figure 5:
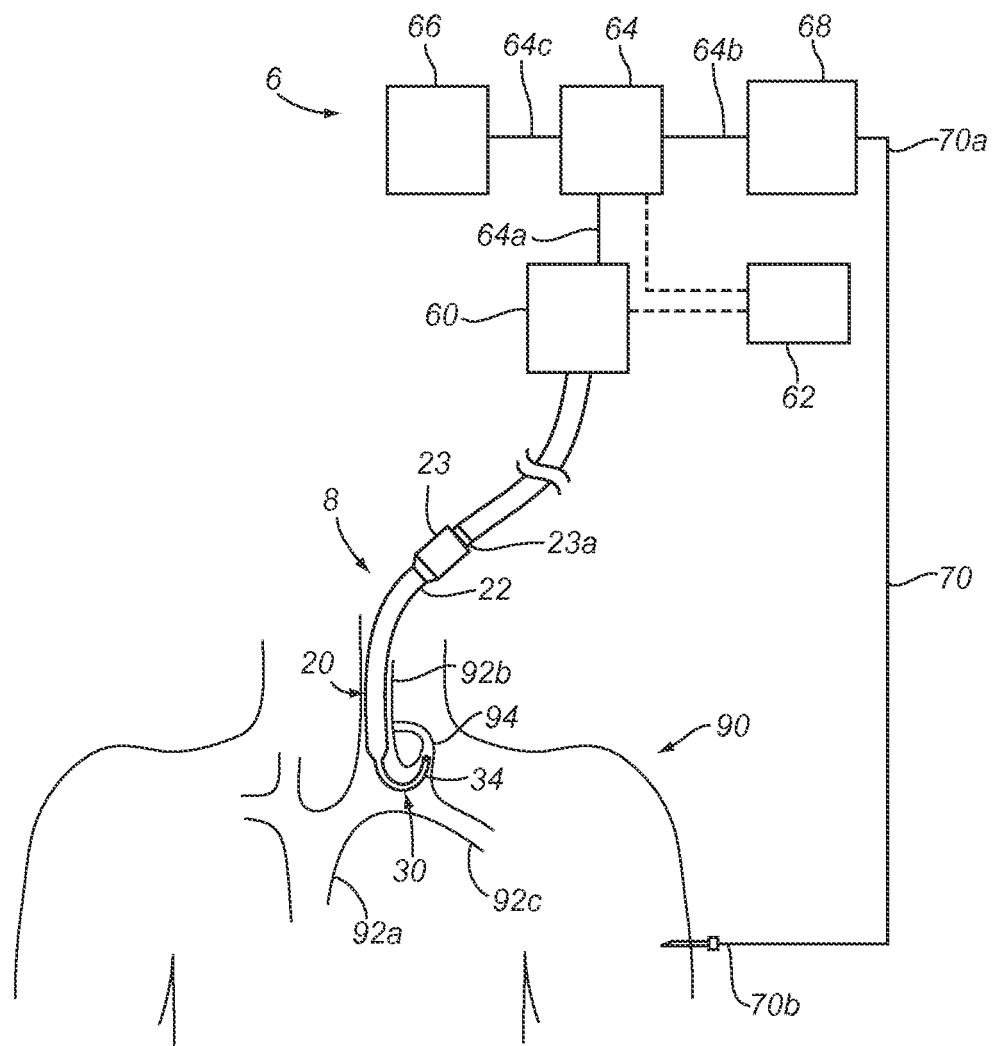
FIG. 5 is a detail of a patient's body showing a schematic of an exemplary system for accessing the lymphatic system of the patient including an apparatus, such as that shown in FIGS. 1-2B.

Generally, the proximal and distal portions 20, 30 of the catheter 10 have different dimensions and/or properties. For example, the proximal portion 20 may have a substantially straight shape in a relaxed state, yet may be sufficiently flexible to be introduced into a patient's body 90, e.g., sufficiently flexible to be introduced into the venous system from a percutaneous access site, such as via a left or right internal or external jugular vein, subclavian vein, axillary vein, or other percutaneous access site. In an exemplary embodiment, access may be gained from the left internal jugular vein 92b to approach the junction of the left internal jugular vein 92b and left subclavian vein 92c, as shown in FIG. 5. The distal portion 30 may have a curvilinear shape in a relaxed state, e.g., a simple curved shape or a more complicated shape including one or more curved and/or straight sections, which may facilitate introduction of the distal portion 30 into the thoracic duct 94, e.g., from the jugular vein 92b, as described further below.

In addition or alternatively, the proximal portion 20 may be substantially longer than the distal portion 30, e.g., to allow the proximal portion 20 to be introduced into the patient's body from an access site, e.g., into the left internal jugular vein 92b, and manipulated to introduce the distal portion 30 into the thoracic duct 94. For example, as shown in FIG. 1, the proximal portion 20 may include a proximal end 22 including a handle or hub 23, and a distal end 24 coupled or otherwise including a transition 25 to the distal portion 30. In exemplary embodiments, the proximal portion 20 may have a length from the handle 23 to the transition 25 between about three and one hundred twenty centimeters (3.0-120 cm), or alternatively between about three and thirty centimeters (3.0-30.0 cm), and may have an outer diameter or other maximum cross-section between about one and seven millimeters (1.0-7.0 mm), or alternatively between about one and three millimeters (1.0-3.0 mm).

The transition 25 may include a tapered shape, as shown, an abrupt step-down shape (not shown), and the like to transition between the proximal and distal portions 20, 30. If the proximal and distal portions 20, 30 are formed from different materials, the transition 25 may connect the different materials together, e.g., by bonding with adhesive, fusing, sonic welding, heat forming, and the like.

The distal portion 30 may have a proximal end 32 extending distally from the transition 25, e.g., aligned substantially axially with the proximal portion 20, and a distal end 34 terminating in a distal tip 35. In exemplary embodiments, the distal portion 30 may have a length from the proximal end 32 to the distal tip 35 between about one and ten centimeters (1.0-10.0 cm), and may have an outer diameter or other maximum cross-section between about half to five millimeters (0.5-5.0 mm), or alternatively between about half and two millimeters (0.5-2.0 mm). Thus, the distal portion 30 may be substantially shorter than the proximal portion 20, e.g., such that the proximal portion 20 may extend from a percutaneous access site (not shown) into the junction of the left internal jugular vein 92b and the left subclavian vein 92c, and the distal portion 30 may simply curve and enter the thoracic duct 94, as described further elsewhere herein. The proximal portion 20 may be sufficiently long such that enough redundancy exists in the segment between the distal tip 35 and the vascular entry point to accommodate normal patient movement without dislodging the distal tip 35 from within the thoracic duct 94.

The distal portion 30 may have a substantially uniform outer diameter between the proximal end 32 and the distal tip 35, or the diameter may vary, e.g., tapering at or adjacent the distal tip 35 to provide a substantially atraumatic distal tip 35.

In addition, the distal portion 30 may have a flexibility greater than the proximal portion 20. For example, the proximal portion 20 may have sufficient column strength, stiffness, torque, and the like such that the proximal portion 20 may be manipulated from the handle 23 without substantial risk of the distal end 24 of the proximal portion 20 buckling or kinking, while providing sufficient flexibility to accommodate introduction into curved vessels within the patient's body. In exemplary embodiments, the proximal portion 20 may have a substantially rigid or semi-rigid proximal end 22, e.g., to facilitate advancement of the distal portion from the handle 23, while the distal end 24 may be semi-rigid or flexible. Moreover, the device properties may be optimized to responsively translate manipulation of the proximal end 22 into movement of the distal portion 30, e.g. by means of rotation, torque, angular manipulation, withdrawal, and/or advancement.

To this end, the apparatus 8 may include one or more elements (not shown) embedded in and/or attached along at least part of its length to resist bending in at least one predetermined plane and/or cause preferential bending in another, generally orthogonal, plane. In an exemplary embodiment, the plane resistant to bending may be oriented approximately orthogonally to a curvilinear shape of the distal portion 30, e.g. to minimize lateral and/or twisting movement of the distal portion 30 when the device is rotated and/or otherwise manipulated to introduce the distal portion 30 into the thoracic duct 94. Bend resistant elements (not shown) may include one or more wires, threads, cables, beams, and/or other profiles that resist compression, elongation, flexion and/or rotation.

The distal portion 30 may be substantially flexible, e.g., biased to the curvilinear shape when free from external forces, yet flexible to accommodate bending, compressing (of the distal tip 35 towards the proximal portion 20), and/or other movement of the distal portion 30 to facilitate introducing the distal tip 35 into the thoracic duct. In exemplary embodiments, the distal portion 30 may be formed from PEBAX, urethane, silicone, and/or other soft and/or flexible materials, e.g., having substantially uniform properties along the length of the distal portion 30, or becoming progressively (or otherwise) softer and/or more flexible from the proximal end 32 to the distal tip 35. The proximal and distal portions 20, 30 may be formed from different materials to provide the desired flexibility. For example, the proximal portion 20 may include a reinforcement layer, e.g., braiding and the like between inner and outer layers (not shown), while the distal portion 30 may simply include a single layer or vice versa. Alternatively, a different reinforcing layer (e.g. braid, coil, stent-like structure or other scaffolding) may be used in the proximal and distal portions 20, 30.

In addition or alternatively, relative flexibility may be obtained by providing different wall thicknesses, e.g., from the same or different materials. For example, as shown in FIGS. 2A and 2B, the proximal portion 20 may have a relatively larger wall thickness than the distal portion 30, which may enhance relative flexibility of the distal portion 30. In exemplary embodiments, the wall thickness of the proximal portion 20 may be between about 0.1 and three millimeters (0.1-3.0 mm), while the wall thickness of the distal portion 30 may be between about 0.1 and two millimeters (0.1-2.0 mm).

As shown in FIG. 1, the distal portion 30 may include multiple substantially straight sections between curved sections, e.g., to provide a "hook" shape having an overall angle of curvature equal to or greater than ninety degrees, e.g., between about ninety and three hundred sixty degrees)(90-360°, or between about ninety and one hundred fifty degrees)(90-150°. Such radii of curvature may facilitate introduction into the thoracic duct 94, which may connect near the junction of the jugular, subclavian, and brachiocephalic veins 92 at an acute angle, such that a radius of curvature greater than ninety degrees (90°) may be necessary to align the distal tip 35 with the thoracic duct 94 when the proximal portion 20 is within the left internal jugular vein 92b, as described further elsewhere herein.

Figures 3A, 3B, 3C:
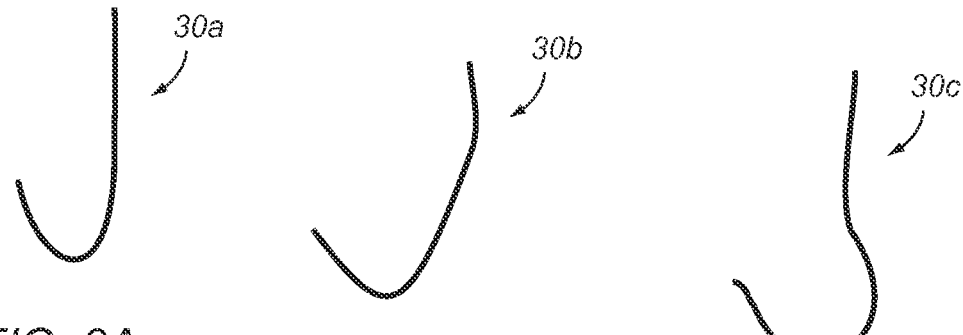
FIGS. 3A-3C are schematic views showing alternative relaxed shapes for the distal portion of an apparatus, such as that shown in FIG. 1.

In an alternative embodiment, shown in FIG. 3A, the distal portion 30a may include a single substantially continuous radius of curvature approaching one hundred eighty degrees (180°). In a further alternative, shown in FIG. 3B, the distal portion 30b may have a more complicated curvilinear shape, e.g., including a first straight section between a bend and a radiused section ending in a substantially straight distal tip (which may carry a balloon, not shown). In yet another alternative, shown in FIG. 3C, the distal portion 30c may include a continuous curved shape including a first bend in an opposite direction to the main radius of curvature of the distal portion 30c. Such shapes may orient the distal tip 35 of the catheter 10 back towards the proximal end 22 with the distal tip 35 defining a desired angle relative to the longitudinal axis 18 within the proximal portion 20.

In still another alternative, the distal portion 30 may include a curved section of constant or variable radius having an arc angle of between about zero and three hundred sixty degrees (0°-360°) and a radius of curvature between about one and fifteen millimeters (1.0-15.0 mm). Further alternatively, the distal portion 30 may include one or more discrete bends, creating a distal shape having a width between about two and thirty millimeters (2.0-30.0 mm). More generally, any of the foregoing shapes may be optimized to locate the distal tip 35 at or near the thoracic duct ostium and simultaneously align the tip vector with the entry vector of the thoracic duct 94. Furthermore, the shape of the distal portion 30 may be sufficiently resilient to return to its pre-set shape, e.g. after introduction through a sheath, repeated manipulation, and the like. Further alternatively, the apparatus 8 may included at least one more proximally located curved section (not shown) adapted to bend or unbend with and thereby accommodate changes in path length from the access site (e.g. the entry into the left internal jugular vein 92b) to the thoracic duct 94, e.g., as may occur with patient movement.

Optionally, the distal portion 30 may include one or more features to facilitate identification and/or localization of the distal portion 30, e.g., the balloon 50 and/or distal tip 35, within a patient's body using external imaging. For example, one or more echogenic features, may be provided on or in the wall of the balloon 50 and/or on the distal tip 35, which may facilitate monitoring the distal portion 30 using ultrasound imaging. Such exemplary features may include doping or coating with tungsten, tungsten carbide, titanium dioxide, iron oxide, zinc oxide, platinum, gold, barium, bismuth, and/or titanium; echogenic surface modifications such as reflective gratings, surface depression and/or projections; inclusions, for example, of glass particles, air bubbles, and the like, including those described in U.S. Pat. No. 5,921,933, the entire disclosure of which is expressly incorporated by reference herein. Alternatively, radiopaque and/or other markers (also not shown) may be provided to facilitate monitoring the distal portion 30 using fluoroscopy or other external imaging. Further alternatively a balloon 50 and/or a lumen of the apparatus 8 may be filled with one or more materials to enhance external imaging. For example, the balloon 50 may be inflated with air and/or a microbubble solution to aid in visualization under ultrasound.

Returning to FIGS. 1-2B, the catheter 10 may include one or more lumens 26, 27 extending therethrough, e.g., from the proximal end 22 of the proximal portion 20 to the distal portion 30. For example, as shown in FIG. 1, an aspiration or infusion lumen 26 may be provided that communicates with a port 23a in the handle 23 and extends through the entire proximal and distal portions 20, 30 to one or more inlet (or outlet) ports 36 adjacent the distal tip 35. As best seen in FIGS. 2A and 2B, the aspiration lumen 26 may include a relatively large region 26a within the proximal portion 20 and a relatively small region 26b within the distal portion 30. In exemplary embodiments, the proximal region 26a of the lumen 26 may have an inner diameter (or other maximum cross-section) between about one and five millimeters (1.0-5.0 mm), while the distal region 26b may have an inner diameter (or other maximum cross-section) between about 0.1 and three millimeters (0.1-3.0 mm).

The smaller diameter of the distal region 26b may allow the outer diameter of the distal portion 30 to be minimized, e.g., to provide desired flexibility and/or minimize the size of the distal portion 30 to facilitate introduction into the thoracic duct 94, while the larger diameter of the proximal region 26a may allow lymph or other fluids to be drawn through the catheter 10 more easily. For example, the larger diameter over most of the length of the catheter 10 may expose the fluid to lower friction, which may increase flow rate and/or reduce the risk of lysing or otherwise damaging cells or other components of the fluid being aspirated or delivered through the lumen 26 of the catheter 10.

Figures 4A, 4B:
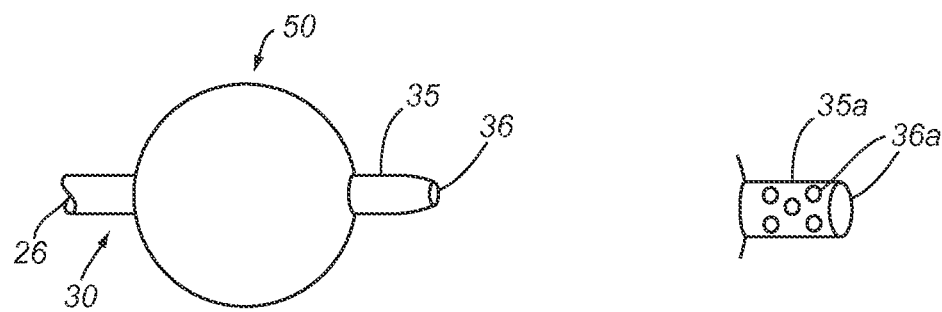
FIGS. 4A-4C are details of alternative embodiments of distal tips that may be provided on an apparatus, such as that shown in FIGS. 1-2B.
Figures 4C, 4D:
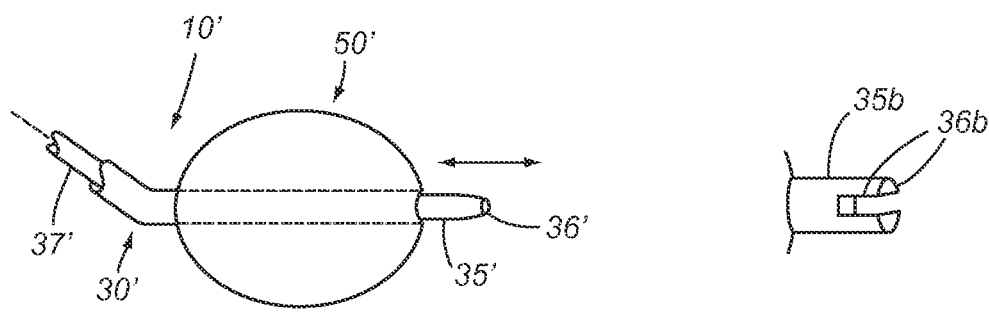
FIG. 4D is a detail of another alternative embodiment of a retractable/advanceable distal tip that may be provided on an apparatus, such as that shown in FIGS. 1-2B.

As shown in FIGS. 2A, 2B, and 4A, the aspiration lumen 26 may communicate with a single inlet port 36 in the distal tip 35, e.g., aligned with the central longitudinal axis 18. Alternatively, multiple inlet ports may be provided on the distal tip, e.g., to reduce the risk of a single or multiple ports becoming occluded with fluid or debris and/or contacting and sucking the wall of the thoracic duct or other body lumen against the distal tip 35, which may otherwise prevent fluid from being drawn into the lumen 26. For example, as shown in FIG. 4B, the distal tip 35a may include a plurality of side ports in addition to the axial inlet port 36a, or, as shown in FIG. 4C, one or more slots (two shown) may be provided that extend partially from the axial inlet port 36b.

In addition, turning to FIG. 2C, the catheter 10 may include an inflation lumen 27, e.g., extending through the proximal and distal portions 20, 30 and communicating with an interior of the balloon 50. The inflation lumen 27 may communicate with a port 23b on the handle 23, shown in FIG. 1, which may allow a source of inflation and/or vacuum, e.g., a syringe and the like (not shown), to be coupled to the catheter 10 and communicate with the interior of the balloon 50, e.g. to allow the balloon 50 to be inflated and collapsed, as described elsewhere herein. Alternatively, another expanded member, e.g., a mechanically expandable frame and the like (not shown, see, e.g., FIGS. 9A-9C), may be provided on the distal portion 30 instead of the balloon 30. In this alternative, a mechanical actuator, e.g., a slider, wheel, and the like (also not shown, may be provided on the handle 23 that is coupled to the frame or other expandable member for directing the expandable member between collapsed and enlarged configurations.

Optionally, the catheter 10 may include one or more additional lumens, if desired. For example, an infusion lumen (not shown) separate from the aspiration lumen 26 may be provided, which may allow infusion of fluids or agents through the catheter 10 to one or more outlets (also not shown) on the distal portion 30, independent of aspiration or removal of fluid through the lumen 26. Infusion of fluids may be into the thoracic duct 94 or into the vein(s) at any point along the course of the catheter 10. Infused fluids may include at least some part or all of fluids aspirated by means of the same catheter. Further alternatively, at least some part or all of fluids aspirated may be infused back into the patient through the annular space between the apparatus 8 and an introducing catheter or sheath (not shown) through which the apparatus 8 passes. In addition, a guidewire lumen and/or a stylet lumen (not shown) may be provided that extends through the proximal portion 20 into the distal portion 30, e.g., for at least partially straightening and/or supporting the distal portion 30 during introduction into a patient's body, as described elsewhere herein.

Figure 6:
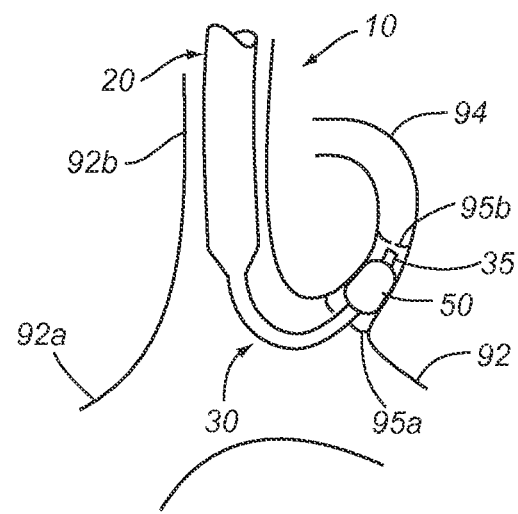
FIG. 6 is a detail of a patient's body, showing the distal portion of a catheter positioned within a thoracic duct of the patient and with a balloon thereon inflated to substantially isolate the thoracic duct from the patients venous system.

Turning to FIGS. 5 and 6, the apparatus 8 may be used to perform a medical procedure within the patient's body 90 that includes accessing the thoracic duct 94, which may be related to any of the conditions and/or treatments described elsewhere herein. Initially, the catheter 10 may be introduced into the patient's body 90, e.g., into the venous system from a percutaneous access site, such as the left or right internal or external jugular, subclavian, axillary, anterior cubital, or femoral veins.

To facilitate introduction and/or navigation of the catheter 10, one or more other devices may be used in conjunction with the catheter 10, if desired. For example, in one embodiment, a guidewire (not shown) may be introduced and advanced from the percutaneous access site, through any intervening vessels into the junction of the left internal jugular vein 92b and left subclavian vein 92c, and into the thoracic duct 94. The guidewire may be backloaded into the inlet port 36 of the distal portion 30 and through the aspiration lumen 26 (or through a separate lumen, e.g., a dedicated guidewire lumen, not shown, if provided on the catheter 10). The catheter 10 may then be advanced over the guidewire into the access site and intervening vessels, and at least the distal tip 35 of the distal portion 30 may be introduced into the thoracic duct 94.

In addition or alternatively, other devices may be used to at least partially straighten and/or otherwise support the distal portion 30 of the catheter 10. For example, a stylet (not shown) may be positioned within the catheter 10, e.g., within the aspiration lumen 26 or a separate lumen (not shown) such that the stylet enters at least partially into the distal portion 30, thereby directing the distal portion 30 from its relaxed curvilinear shape to a less curved or substantially straight configuration (not shown) and/or otherwise supporting the distal portion 30 from buckling or kinking. The distal portion 30 may then be introduced through the access site and any intervening vessels until the distal tip 35 is located adjacent the thoracic duct 94, e.g., within the junction of the jugular and subclavian veins 92b, 92c. The stylet may be sufficiently flexible to accommodate introducing the distal portion 30 through any bends or tortuous anatomy encountered between the access site and the thoracic duct 94. Once the distal tip 35 is located adjacent the thoracic duct 94, e.g., within the junction of the left internal jugular vein 92b and the left subclavian vein 92b, the stylet may be removed, thereby allowing the distal portion 30 to return towards its relaxed, curvilinear configuration. Alternatively, one or more shaped stylets may be used to accentuate, alter, essentially create the shape of the distal portion 30. Further, a stylet may be used to direct the distal portion 30 toward and/or into the thoracic duct 94, e.g., by independent and/or co-manipulation (e.g. twisting, advancing, retracting) of the stylet and the catheter 10. For example a stylet may be shaped and positioned so as to direct the distal portion 30 toward the thoracic duct 94. The apparatus 8, including distal portion 30, may then be advanced along the trajectory created by the stylet in order to approach and/or cannulate the thoracic duct 94. In this case, the distal portion 30 may be substantially straight and compliant and/or may comprise a curvilinear shape.

In another alternative, a sleeve, sheath, cover, and the like (also not shown) may be provided over the catheter 10 until the distal portion 30 is sufficiently covered, e.g., to at least partially straighten and/or support the distal portion 30. The distal portion 30 may then introduced into the patient's body 90 until the distal tip 35 is disposed adjacent the thoracic duct 94, whereupon the cover may be removed to expose and release the distal portion 30, again thereby allowing the distal portion 30 to return towards its relaxed, curvilinear configuration.

With the distal portion released or exposed within the junction, the proximal portion 20 of the catheter 10 may then be manipulated, e.g., advanced and/or retracted, rotated, and the like until the distal tip 35 enters the thoracic duct 94, as shown in FIG. 5. For example, without a guidewire, the catheter 10 may be manipulated until the distal portion 30 "hooks" the ostium of the thoracic duct 94. Because of the soft and/or flexible nature of the distal portion 30, such manipulation may be completed without substantial risk of perforation or other damage to the vessels. In addition, given that the thoracic duct 94 may extend at an angle almost one hundred eighty degrees relative to the left internal jugular vein 92b, the angle of the distal portion 30 may facilitate orienting the distal tip 35 "backwards" towards the ostium of the thoracic duct 94.

Once the distal tip 35 is placed within the ostium of the thoracic duct 94, the catheter 10 may be retracted, advanced, or otherwise manipulated to direct the distal portion 30 further into the thoracic duct 94. For example, if the catheter 10 is to be introduced into the left internal jugular vein 92b, as shown in FIG. 5, the length of the catheter 10 may be substantially shorter than most catheters, thereby providing a more direct relationship of movement between the proximal end 22 and the distal portion 30 since the catheter 10 is less likely to twist, compress, stretch, and the like between the proximal end 22 and the distal portion 30.

If the catheter 10 is manipulated to place the distal tip 35 at the ostium of the thoracic duct 94, the catheter 10 may simply be retracted (e.g., upwardly) to pull the distal tip 35 up into the thoracic duct 94, e.g., as shown in FIG. 6. In an exemplary embodiment, the distal portion 30 may pass through the terminal valve 95a of the thoracic duct 94 until the balloon 50 is positioned between the terminal valve 95a and the next valve 95b within the thoracic duct 94. The balloon 50 may then be inflated to engage the wall of the thoracic duct 94 and substantially seal and/or isolate the thoracic duct 94 from the veins 92. The length of the balloon 50 may be adapted to fit between the terminal valve 95a and next valve 95b, having a length between 2 and 20 mm or alternatively between 5 and 10 mm.

Optionally, navigation to the thoracic duct 94 may be aided using external imaging, such as ultrasound imaging. For example, as described elsewhere herein, the distal portion 30 of the catheter 10 may include one or more echogenic features, which may facilitate identification and monitoring the balloon 50 and/or the distal tip 35. Because the thoracic duct 94 is located near the surface, i.e., close to the patient's skin, an ultrasound imaging device placed on or near the patient's skin may provide high resolution visualization of the region including the thoracic duct 94 and adjacent veins 92 to facilitate monitoring the distal portion 30 until the distal tip 35 and balloon 50 are positioned as desired.

Pertaining specifically to ultrasound guided placement of the catheter, it is desirable to view the thoracic duct and its terminal valve in a longitudinal plane relative to the body such that the proximal 20 and distal 30 portions of the catheter can be seen the same field of view and same plane as the terminal valve 95a and first segment of the thoracic duct 94. Achieving this desirable view may be facilitated by identification of the venous confluence (i.e. jugular, subclavian, and innominate veins) in an axial plane followed by rotation of the ultrasound transducer to create the desired longitudinal plane. Identification of the thoracic duct 94 may be confirmed by visualizing a terminal valve 95a, chylous or turbulent outflow of lymph into the venous confluence, or subsequent lymphatic valves (e.g., 95b, etc.) and associated sacculations of intervening thoracic duct segments. After identification of the thoracic duct 94 has been confirmed and the distal portion 30 has been advanced into the venous confluence, it is desirable to maintain the longitudinal field of view, as described, throughout the placement procedure, including the following steps: 1) intubation and traversal of the terminal valve 95a by the distal tip 30, 2) passage of the uninflated balloon 50 past the terminal valve 95a, and 3) inflation of the balloon 50. It may be desirable to infuse a small amount of air to fill an inflation lumen 27 without substantially inflating the balloon 50 in order to improve visualization of the apparatus 8 along its length under ultrasound. Removal of the apparatus from the body need not involve ultrasound visualization and can generally be completed by fully deflating the distal balloon and removing the catheter through the skin. However, ultrasound may be useful to confirm functionality of the terminal valve 95a and/or exclude damage to the vasculature and/or thoracic duct 94 post-procedure.

In addition or alternatively, tactile feedback and/or manipulation may be used to facilitate positioning the distal portion 30. For example, given the close proximity of the thoracic duct 94 and neighboring veins 92 to the skin, it may be possible to feel the catheter 10 by placing the user's fingers on the patient's overlying skin and pressing against the skin and intervening tissues. Such pressure may also be used to physically manipulate the distal portion 30, e.g., in addition to manipulation of the proximal end 22, to direct the distal tip 35 into the thoracic duct 94.

In addition or alternatively, other imaging may be used, such as fluoroscopy, MRI, CT, and/or direct visualization, e.g., using an imaging element carried on the distal portion 30 of the catheter 10. Exemplary imaging elements and methods for using them are disclosed in U.S. Publication Nos. 2011/0034790, 2007/0015964, 2006/0084839, and 2004/0097788, the entire disclosures of which are expressly incorporated by reference herein.

Optionally, additional methods may be used to facilitate introducing the distal tip 35 and balloon 50 through the terminal valve 95a, e.g., instead of simply pushing the distal tip 35 through the valve 95a. For example, the terminal valve 95a may be monitored using external imaging or otherwise monitored to coordinate timing of movement of the terminal valve 95a with physiological events, e.g., heart rate, and the like, until the terminal valve 95a naturally opens, whereupon the distal tip 35 may be advanced through the open valve 95a into the thoracic duct 94. Alternatively, the user may trigger opening of the terminal valve 95a, e.g., by increasing lymph within the patient's body, for example, by squeezing tissue in the arm or leg.

In another alternative, a negative pressure may be created within the junction, e.g., by aspirating into the catheter 10 or otherwise, with the resulting vacuum causing the terminal valve 95a to open and allow the distal tip 35 to be advanced into the thoracic duct 94. In other alternatives, the user may simply periodically probe the terminal valve 95a by gently advancing the distal tip 35 against the valve 95a and/or by rotating the catheter 10 to screw the distal tip 35 through the valve 95a. Further alternatively, the balloon 50 (or other distal expandable member) may be at least partially expanded to assist in centering the distal tip 35 in or near the ostium in order to more easily cross the valve 95a. The distal tip 35 may be adapted to extend beyond the balloon 50 by between 1 and 10 mm or alternatively between 1 and 5 mm in order to engage the thoracic duct 94 and/or its terminal valve 95a while the balloon 50 is at least partially inflated.

In yet another alternative, a helical tip member (not shown) may be provided on the distal portion 30 that extends from the distal tip 35, which may be rotated to guide the distal tip 35 through the terminal valve 95a. In these alternatives, the distal portion 30 may pass through the terminal valve 95a until the balloon 50 is positioned between the terminal valve 95a and the next valve 95b within the thoracic duct 94. The balloon 50 may then be inflated to engage the wall of the thoracic duct 94 and substantially seal and/or isolate the thoracic duct 94 from the veins 92.

With the balloon 50 expanded to substantially isolate the thoracic duct 94, fluid may be aspirated into the lumen 26 of the catheter 10 and collected, e.g., as described elsewhere herein, fluid may be delivered into the thoracic duct 94, and/or other desired procedures may be performed via the thoracic duct 94.

In an alternative embodiment, shown in FIG. 4D, the catheter 10' may include a movable distal tip 35,' which may be directed axially closer to or away from the balloon 50.' For example, the balloon 50' may be attached to the distal end of an outer tubular member 30,' and an inner tubular member 37' may extend through the outer tubular member 30' and the balloon 50,' and terminate in the distal tip 35.' Thus, movement of the inner tubular member 37' relative to the outer tubular member 30' may move the distal tip 35' relative to the balloon 50.' In this alternative, the balloon 50' may serve to substantially center the distal tip 35' relative to the valve(s) 95 within the thoracic duct 94 (not shown in FIG. 4D), e.g., such that the distal tip 35' may be advanced or retracted as desired relative to the valve(s) 95 to facilitate access, removal of fluid, and/or performing other procedures within the thoracic duct 94.

Optionally, the suction pressure used to aspirate lymph within the thoracic duct 94 may be adjusted, e.g., to substantially match the individual patient's maximum lymph flow. If the patient lymph flow changes over time, this method anticipates adjustment of pressure over time, both decreasing suction pressure over time, and increasing suction pressure over time, as desired.

In another option, fluids or other substances may be infused into the thoracic duct 94 or vein via the catheter 10, if desired. For example, one or more of the following may be infused: blood contaminated lymph, lymph with greater concentrations of desired substances, and the like.

In another embodiment (not shown), the catheter may include a distal end and balloon sized to be introduced into the thoracic duct. For example, the distal end may be advanced beyond a valve in the thoracic duct such that the balloon may be inflated beyond the valve. In addition or alternatively, the catheter may include one or more other features for securing and/or sealing distal to a valve, including one or more compliant rings, radial filaments/brushes, and/or other passive fixation devices (not shown) that may at least partially resist retraction or avoid spontaneous dislodgement of the catheter during use. In addition or alternatively, active fixation, such as suction, may be used to substantially fix the distal end of the catheter at a desired location, e.g., within the thoracic duct.

Figure 7:
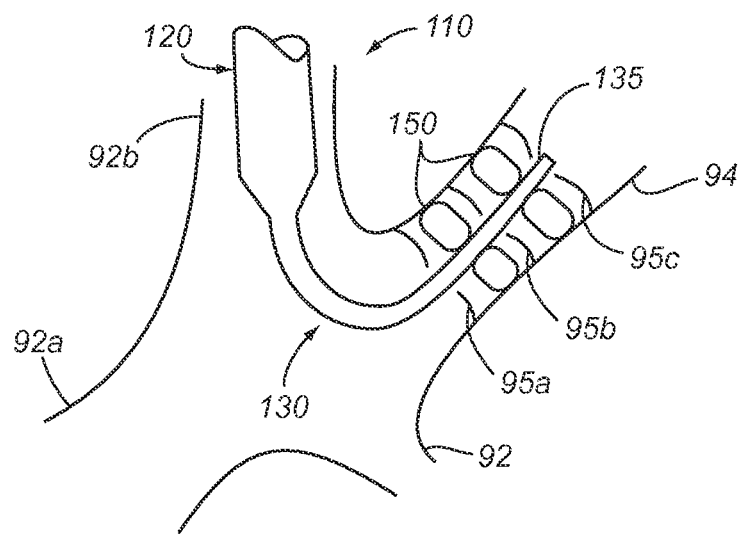
FIG. 7 is a detail of a patient's body, showing a distal portion of another exemplary embodiment of an apparatus with a pair of balloons expanded within a thoracic duct of the patient on either side of a valve within the thoracic duct.

Turning to FIG. 7, another embodiment of a catheter 110 is shown that includes a pair of balloons 150 spaced apart axially from one another on a distal portion 130 of the catheter 130. The balloons 150 may communicate with a single inflation lumen (not shown) such that the balloons 150 may be inflated and/or collapsed substantially simultaneously. Alternatively, the balloons 150 may communicate with separate inflation lumens (also not shown) such that the balloons 150 may be inflated and/or collapsed independently of one another.

As shown in FIG. 7, a distal tip 135 of the catheter 110 may be introduced into the thoracic duct 94 until the balloons 150 pass beyond the terminal valve 95a. Optionally, as shown, the balloons 150 may be spaced apart sufficiently from one another such that the balloons may be provided on either side of the next valve 95b within the thoracic duct 94. Such an arrangement of balloons 150 may provide enhanced stability for the distal portion 130 and/or improved sealing of the thoracic duct 94.

Optionally, the balloons 150 may be configured such that the balloons 150 may be positioned with a valve 95b located between the balloons 150. When the balloons 150 are inflated, they may squeeze or otherwise engage the valve 95b to enhance sealing of the thoracic duct 94 using the valve 95b in addition to the balloons 150 engaging the wall of the thoracic duct 94. In another option, the balloons 150 may be positioned on either side of the terminal valve 95a (not shown) such that the proximal balloon engages the ostium of the thoracic duct 94 outside the terminal valve 95a, which may reduce the risk of blood entering the thoracic duct 94 from the veins 92. Further alternatively, the balloons 150 may be slidably disposed relative to one another (not shown) such that they may be brought together or moved apart, e.g., to capture and/or release a valve positioned between them. Further alternatively, one or more balloons may include different surface properties, e.g. a lubricious distal surface (e.g., using a hydrophilic coating, lubrication, surface features, and the like), e.g., to facilitate valve crossing and a less lubricious proximal surface to, e.g. to decrease the chance of inadvertent removal.

Figure 8:
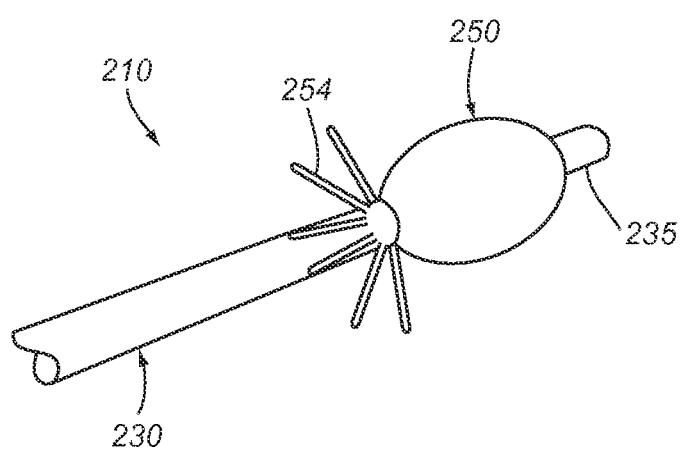
FIG. 8 is a detail showing a distal portion of another embodiment of a catheter including a plurality of expandable tines adjacent a balloon for anchoring the distal portion relative to a thoracic duct.

Turning to FIG. 8, still another embodiment of a catheter 210 is shown that includes a plurality of tines 254 on the distal portion 230 adjacent the balloon 250. The tines 254 may be biased to expand outwardly, but may be compressible inwardly, e.g., using an external sleeve or other constraint (not shown), which may be removed, e.g., after positioning the balloon 250 at a desired position within a thoracic duct (also not shown). When the tines 254 are deployed, they may engage the wall of the thoracic duct to anchor the distal portion 230 to prevent movement even if the balloon 250 is collapsed. The tines 254 may include substantially blunt free ends to engage the thoracic duct without penetrating or damaging the wall, or may include sharpened tips and/or barbs (not shown), which may be substantially permanently or indefinitely engage the wall of the thoracic duct. Thus, this embodiment may be used to secure the catheter 210 substantially indefinitely, e.g., for a long-term implant that is used to intermittently isolate the thoracic duct by expanding the balloon 250, e.g., to collect lymph. When not needed, the balloon 250 may be collapsed allowing normal function of the thoracic duct. If desired, the catheter 210 may be removed, e.g., by directing a sheath or other tubular member (not shown) into the thoracic duct to recapture and collapse the tines 254.

Figure 9A:
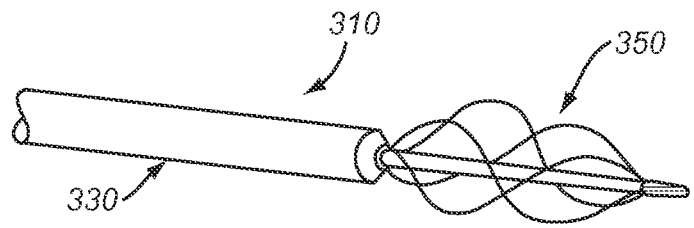
FIGS. 9A-9C are side and ends views of yet another embodiment of a catheter including a mechanically expandable member that is expandable from a collapsed configuration (FIG. 9A) to an enlarged configuration (FIGS. 9B and 9C) for isolating a thoracic duct.
Figure 9B:
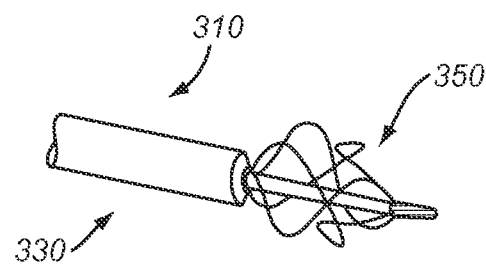
Figure 9C:
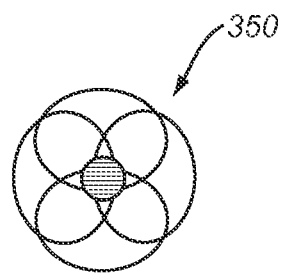

Turning to FIGS. 9A-9C, another embodiment of a catheter 310 is shown that includes an expandable frame 350 on a distal portion 330 including a set of wires or struts that may be manipulated from a proximal end (not shown) of the catheter 310. For example, an actuator on the proximal end (not shown) may be activated to direct the frame from a collapsed configuration (shown in FIG. 9A) to an enlarged configuration (shown in FIG. 9B). The size of the frame 350 may be sufficient to engage a wall of a thoracic duct when the distal portion 330 is introduced into the thoracic duct, as described elsewhere herein.

As shown in FIG. 9C, the frame 350 may carry a nonporous membrane that may be directed across the thoracic duct when the frame 350 is expanded to substantially seal the thoracic duct. Thus, the frame 350 may operate similar to the balloons described elsewhere herein, except that the frame 350 is mechanically actuated rather using fluid to inflate and collapse the balloons.

Turning to FIG. 5, the apparatus 8 may be part of a system 6 including one or more external components for performing a medical procedure, e.g., which may involve removing lymphatic fluid from the patient's body 90 via the thoracic duct 94, introducing agents or devices (not shown) into the thoracic duct 94, and/or infusing the removed lymphatic fluid, components thereof, and/or other agents into other locations within the patient's body 90. For example, one or more external devices may be provided that are coupled to the proximal end 22 of the catheter 10, e.g., for detecting, separating, collecting, and/or infusing lymphatic fluid and/or other fluids, as described in U.S. Publication No. 2011/0276023, the entire disclosure of which is expressly incorporated by reference herein. The external components may be provided integrated into a single device or may be provided as separate discrete components that are coupled to one another (e.g., along a fluid path, electrically, and/or otherwise).

In the example shown schematically in FIG. 5, the external components include a detector 60, a controller 62, a separator 64, a waste container 66, a storage container 68, and an infusion device 70. One or more of the components may include a pump or source of vacuum or pressure, e.g., for removing fluid from the patient's body and/or delivering fluid into the patient's body 90 via the catheter 10, or infusing fluids via the infusion device 70, as described further below. In alternative embodiments, one or more of the components may be omitted. For example, the catheter 10 may simply be coupled directly to the storage container 68, e.g., with or without a source of vacuum to facilitate collection of lymphatic fluid.

The detector 60 may be coupled to the proximal end 22 of the catheter 10, e.g., to the port 23a on the handle 23, for receiving fluids that are drawn through the lumen 26 of the catheter 10 from the inlet port 36 in the distal tip 35 (not shown in FIG. 5, see, e.g., FIGS. 2A, 2B). The detector 60 may include one or more sensors (not shown), e.g., for distinguishing between lymphatic fluid and blood. In exemplary embodiments, the sensor(s) may include one or more optical sensors (e.g., for detecting the presence of red blood cells by light transmission or reflection characteristics), chemical sensors (e.g., for detecting one or more of pH, oxygen concentration, lactate, leukocyte esterase, and the like), sensors for measuring hematocrit, electrical sensors (e.g., for measuring impedance), mechanical sensors (e.g., for detecting pressure waves, which may differ between the venous system and the thoracic duct; for flow detection, e.g., by Doppler ultrasound), filter devices sized to constituents of whole blood, and the like. In addition or alternatively, a sensor may be provided that is adapted to detect the presence of an exogenous marker introduced into the lymphatic system, such as a dye (e.g., methylene blue), an ingested marker, a fluorescent marker, and the like.

For example, a pump or other source of vacuum or pressure (not shown) within or coupled to the detector 60 may be selectively activated, e.g., by the controller 62 (or alternatively manually by a user, if desired), to remove fluid from the patient's body via the catheter 10 through the detector 60 to the separator 64. The controller 62 may automatically analyze sensor data from the sensors to identify whether the fluid is lymphatic fluid, blood, or other fluid.

For example, if the controller 62 determines that the fluid includes blood, the controller 62 may direct the fluid to the waste container 66, e.g., through the separator 64 or directly. In addition or alternatively, if the controller 62 detects the presence of a significant amount blood in the fluid (based on data from the detector 60 or otherwise) or detects a loss of seal (e.g., due a sudden pressure change in the fluid being removed via the catheter 10), the controller 62 may shut down the pump, close a shut-off valve (not shown) in the detector 60, or otherwise stop flow of fluid from the catheter 10 into the detector 60 and/or the rest of the system 6. This safety mechanism may be active, i.e., shut down automatically, or passive, i.e., merely warn the user.

In an exemplary embodiment, the separator 64 may include a valve (not shown) including an inlet 64a that communicates with the detector 60, a first outlet 64b communicating with the storage container 68, and a second outlet 64c communicating with the waste container 66. The valve may be selectively operable between the first and second outlets 64b, 64c by the controller 62, e.g., to direct undesired fluid, e.g., blood, to the waste container 66, and desired fluid, e.g., lymphatic fluid or components thereof, to the storage container 68. Alternatively, or in addition, the separator 64 may include one or more devices for separating various components of lymphatic fluid, including various types of cells, proteins, electrolytes, water, and/or other constituent parts of lymphatic fluid. For example, water may be substantially separated from other components in order to selectively remove excess water from a patient. As another example, pathologic cells may be selectively separated from other constituents in order to remove pathologic cells from a patient.

In an alternative embodiment, a filter (not shown) may be provided within the detector 60 or separator 64, which may clog in the presence of a predetermined number or concentration of cells, e.g., red blood cells, to prevent the fluid from being delivered into the storage container 68. In a further alternative, coagulation/clotting may be used to prevent flow in the presence of whole blood and its constituents (for example, platelets). For example, a passage through the detector 60 or other external component may be sized to clot spontaneously, a filter may be used where clotting decreases flow, and/or pro-coagulant materials may be used to augment or accelerate a clotting response. In such alternatives, the component of the system 6 designed to prevent flow may be cleanable and/or replaceable, e.g., to allow to resumption of flow after isolation of the thoracic duct 94 is reestablished.

If the controller 62 confirms that the fluid is lymphatic fluid, the controller 62 may activate the separator 64 to direct the lymphatic fluid or components of the lymphatic fluid into the storage container 68. For example, if the entire lymphatic fluid is to be collected, the separator 64 may simply divert the fluid into the storage container 68. Alternatively, it may be desirable to separate certain constituents of the removed fluid, e.g., lymphatic fluid, particular cells, proteins, and the like. For example, the separator 64 may include one or more of a mechanical filtration system, an osmotic gradient system, a concentration gradient system, a centrifuge, and the like to separate the desired components from the rest of the fluid. Once separated, the desired components may be delivered to the storage container 68, while the rest of the fluid is delivered to the waste container 66.

Optionally, the controller 62 or other components of the system 6 may monitor the flow to keep track of the amount of fluid extracted and/or to stop after a predetermined amount of fluid is extracted. In addition or alternatively, the controller 62 may operate the pump, vacuum source, valve, and/or other components of the system 6 periodically or otherwise intermittently, e.g., to allow reaccumulation of fluid within the lymphatic vessels.

In certain cases, it may be desirable to re-infuse all or a portion of the lymphatic fluid removed, for example, all cells and/or proteins (e.g., discard fluid and retain the useful constituents of lymph), only a certain portion of removed cells and/or proteins, (e.g., discard harmful constituents and retain useful constituent), and/or other constituents of the removed lymphatic fluid. One approach may be simply to retain an initial volume of removed fluid that may have a higher concentration of cells, proteins, and the like compared to the subsequent volume removed. For example, there may be a relatively small initial volume of lymphatic fluid in the vessels that, upon sustained drainage, may be repleted with interstitial fluid having relatively few cells. Alternatively, filtration, separation, or other methods may be used to create a desirable portion for reinfusion.

For example, as shown in FIG. 5, an infusion catheter 70 may be provided that includes a proximal end 70a coupled to the storage container 68, and a distal end 70b sized for delivering the stored fluid into the patient's body 90.

In an alternate embodiment (now shown) a separate introducer sheath or catheter may be first advanced into the left internal jugular vein 92b and positioned adjacent the thoracic duct 94. Thereafter the apparatus 8 may be passed through the introducer sheath or catheter and positioned within the thoracic duct 94. A side port on the introducer catheter may be used for infusion of substances including processed or returned lymph, drugs or other agents before, after, or contemporaneously with aspiration of lymph.

Figure 10A:
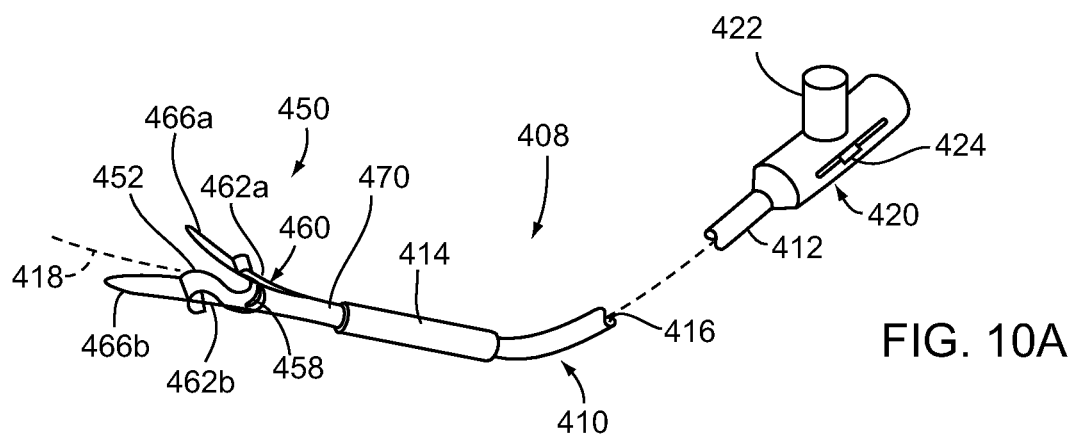
FIGS. 10A and 10B are perspective views of an exemplary embodiment of a catheter including an expandable sealing member carried on a distal portion thereof in a delivery condition (FIG. 10A) and a deployed condition (FIG. 10B).
Figure 10B:
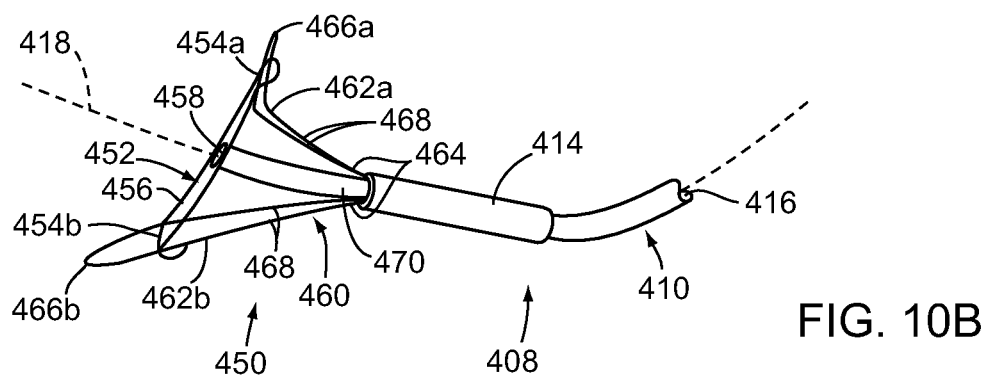
Figure 11:
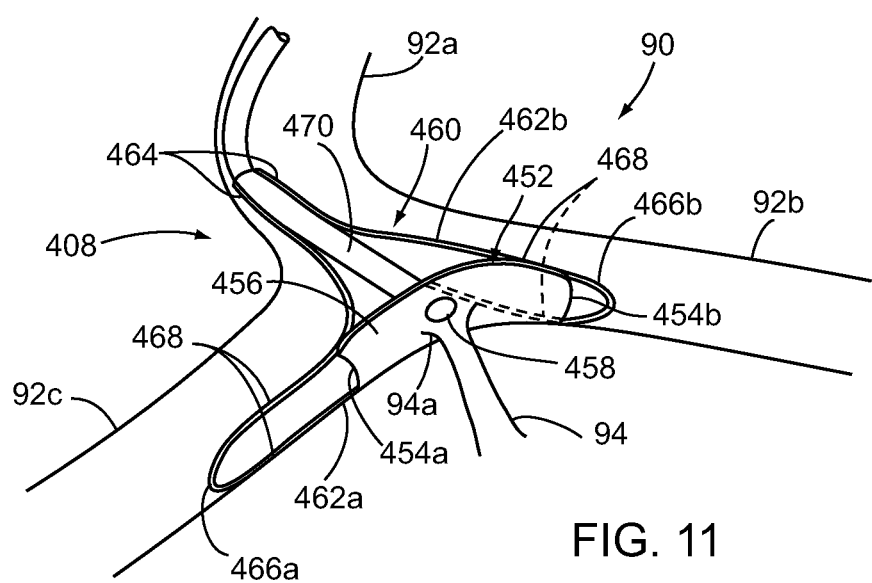
FIG. 11 is a detail of a patient's body, showing the distal portion of the catheter of FIGS. 10A and 10B positioned within the confluence of the internal jugular and subclavian veins with the sealing member expanded and engaged around the outlet of the thoracic duct.

Turning to FIGS. 10A and 10B, another embodiment of an apparatus 408 is shown for accessing and/or isolating the lymphatic system of a patient, e.g., to aspirate or otherwise draw lymphatic fluid from the thoracic duct 94 (e.g., as shown in FIG. 11). Generally, the apparatus 408 includes a catheter, cannula, or other elongate tubular member 410 including an expandable sealing or isolation member 450 carried on a distal end 414 thereof. The sealing member 450 may be configured to engage a vessel wall surrounding the outlet or ostium 94a of the thoracic duct 94, e.g., without entering the ostium 94a, to substantially seal and/or isolate the thoracic duct 94 from the venous system, e.g., from the innominate vein 92a, internal jugular vein 92b, and left subclavian vein 92c adjacent the ostium 94a, as shown in FIG. 11. Optionally, the apparatus 408 may be part of a system, e.g., including one or more additional components, such as one or more guidewires, guide catheters or sheaths, a source of vacuum, an external container, and the like, similar to other embodiments herein.

The catheter 410 generally includes a proximal end 412, a distal end 414 sized for introduction into a patient's body, e.g., into the venous system adjacent the ostium 94a of the thoracic duct 94, and one or more lumens 416 extending between the proximal and distal ends 412, 414, thereby defining a longitudinal axis 418. For example, an aspiration lumen 416 may extend between the proximal and distal ends 412, 414 and may communicate with an aspiration port 458 in the sealing member 450, as described further below.

Optionally, the catheter 410 may also include one or more additional lumens (not shown) extending between the proximal and distal ends 412, 414. For example, an inflation lumen may be provided that communicates from the proximal end 412 to an interior of a balloon (not shown) on the distal end 414, as described elsewhere herein. In addition or alternatively, the catheter 410 may include one or more actuator lumens for receiving one or more pull wires or other actuator members (not shown), also as described elsewhere herein. Further additionally, if desired, an accessory or instrument lumen may be provided that may receive a guidewire or other rail, a stylet, and the like (not shown), e.g., to facilitate introduction and/or manipulation of the catheter 410, as described elsewhere herein.

The catheter 410 may be formed from one or more tubular bodies, e.g., having variable flexibility along its length, if desired. For example, the distal end 414 may be substantially flexible to facilitate introduction through tortuous anatomy. The proximal end 412 may be substantially flexible, semi-rigid, or rigid, e.g., having sufficient column strength to facilitate advancing the distal end 414 through a patient's vasculature by pushing on and/or otherwise manipulated the proximal end 412. Optionally, the distal end 414 may have a relatively stiff distal tip section, e.g., to enhance transferring a distal or other force applied at the proximal end 412 to the sealing member 450, as described elsewhere herein. The catheter 410 may be formed from plastic, metal, or composite materials, e.g., a plastic material having one or more wires, braids, or other reinforcement elements (not shown) embedded or otherwise provided within the wall of the catheter 410, which may prevent kinking and/or buckling of the catheter 410 during advancement or other manipulation.

As shown in FIG. 10A, the catheter 410 may include a handle 420 on the proximal end 412, e.g., to facilitate manipulating the catheter 410. The handle 420 may include one or more ports communicating with respective lumens within the catheter 410, e.g., a side port 422 communicating with the aspiration lumen 416, e.g., to remove lymphatic fluid from the thoracic duct, as described further below. The handle 420 may be molded, machined, or otherwise formed from plastic, metal, or composite material, e.g., providing an outer casing, which may be contoured or otherwise shaped to ease manipulation. The proximal end 412 of the catheter 410 may be attached to the handle 420, e.g., by one or more of bonding, cooperating connectors, interference fit, and the like.

With continued reference to FIGS. 10A and 10B, the sealing member 450 includes a flexible membrane 452 carried by a frame 460 for expanding the sealing member 450 between a delivery condition, e.g., as shown in FIG. 10A, and a deployed condition, e.g., shown in FIG. 10B. For example, the frame 460 may include a pair of opposing arms 462a, 462b that may be foldable or otherwise movable relative to one another, e.g., between a folded or collapsed configuration and an expanded condition for moving the sealing member 450 between the delivery and deployed conditions. As shown, the arms 462 may include first ends 464 coupled to the distal end 414 of the catheter 410 and second free ends 466a, 466b that are spaced apart from one another to define a generally "V" shaped orientation when expanded, as shown in FIG. 10B. The arms 462 may be folded towards one another to reduce the profile of the sealing member 450, e.g., to facilitate introduction into a patient's body, as shown in FIG. 10A.

In an exemplary embodiment, each arm 462 may be defined by a pair of struts 468 that are coupled to the distal end 414 of the catheter at the first end 464 of the arm 462 and to each other to define the second free end 466. As shown, the second free ends 466 may be rounded or otherwise shaped to provide substantially atraumatic tips for the arms 462. The struts 468 may be formed from elastic or superelastic material, e.g., metals, such as Nitinol, stainless steel, and the like, plastics, or composite materials, to accommodate folding of the arms 462 to the collapsed configuration during use, yet biasing the arms 462 to the expanded configuration.

Optionally, the arms 462 may be biased to predetermined shapes based on the anatomy involved during use. For example, a first arm 462a may be biased to an "L" or curved shape, while a second arm 462b may be biased to a substantially straight shape, e.g., as shown in FIG. 10B. In this manner, the "L" shaped first arm 462a may be shaped to engage a wall of the left subclavian vein 92c while the second arm 462b may be received in the internal jugular vein 92b to seat the membrane 452 against the vessel wall surrounding the ostium 94a of the thoracic duct 94, as described further below.

The arms 462 may be biased to the generally "V" shaped expanded configuration shown in FIG. 10B, yet may be resiliently folded inwardly towards one another to define a smaller internal angle between the arms 462 in the collapsed configuration, e.g., as shown in FIG. 10A, when the catheter 410 is loaded into a guide catheter or other delivery sheath (not shown) used to introduce the catheter 410 into a patient's body. Alternatively, the catheter 410 may include a sleeve (not shown) on the distal end 414 that may be advanced and retracted relative to the frame 460 from the proximal end 412, e.g., using an optional actuator 424 on the handle 420 as shown in FIG. 10A. For example, the actuator 424 may be slidable proximally to retract the sleeve to expose and expand the frame 460 and distally to at least partially cover and fold the frame 460 inwardly towards the collapsed configuration. In another alternative, the first ends 464 of the arms 462 may be coupled to one or more pull wires or other actuator members (not shown) extending into the distal end 414 of the catheter 410 rather than to the distal end 414 itself. In this alternative, the actuator member(s) may be actuated from the proximal end 412 (e.g., by sliding the actuator 424) to retract the frame 460 at least partially into the distal end 414 and/or expose the frame from the distal end 414.

With continued reference to FIGS. 10A and 10B, the membrane 452 may be a flexible sheet or other relatively thin member coupled to the arms 462, e.g., adjacent the second free ends 466. For example, opposite ends 454a, 454b of the membrane 452 may be attached to respective arms 462s, 462b such that the membrane 452 may be folded inwardly when the arms 462 are directed to the collapsed configuration and stretched or otherwise directed into a curved shape when the arms 462 are directed to the expanded configuration. In exemplary embodiments, the ends 454 of the membrane 452 may be attached to the arms 462 by one or more of bonding with adhesive, sonic welding or other fusing, stitching with sutures or other filaments (not shown), clips, and the like. For example, the ends 454 of the membrane 452 may be wrapped around cross-struts (not shown) extending between the struts 468 of each respective arm 462 and attached to the contacted membrane material. Alternatively, each of the corners of the membrane 452 may be attached to respective struts 468 of the arms 462.

When the membrane 452 is in the deployed condition, the membrane 452 may define a concave outer surface 456 oriented away from the distal end 414 of the catheter 410. In the embodiment shown in FIG. 10, in the deployed condition, the membrane 452 extends transversely relative to the longitudinal axis 418 of the catheter 410, e.g., such that a line extending between the opposite ends 454 of the membrane 452 are generally perpendicular or otherwise transverse to the longitudinal axis 418, e.g., while the concave shape of the outer surface 454 intersects the longitudinal axis 418.

In an exemplary embodiment, the membrane 452 may define an arcuate or curved shape between the opposite ends 454, thereby defining the concave outer surface 456. The width of the membrane 452 may be substantially uniform between the ends 454 or the central region of the membrane 452 between the ends 454 may be wider than the ends 454. In addition, the membrane 452 may be substantially flat across its width or may have an additional arcuate cross-sectional shape across its width, e.g., such that the longitudinal edges of the membrane 452 are closer to the distal end 414 of the catheter 410 than a central section between the longitudinal edges. For example, the center of radius of the arcuate shape may be located between the membrane 452 and the distal end 414 of the catheter 410, while a center of radius of the concave surface 456 between the ends 454 may be distally beyond the membrane 452. In this manner, the shape of the membrane 452 may be designed to conform to the anticipated shape of the vessel wall surrounding the outlet 94a of the thoracic duct 94. For example, the radius of curvature of the arcuate shape may correspond to the typical radius of the internal jugular and subclavian veins adjacent the outlet 94a and the concave radius of the membrane 452 between its ends 454 may correspond to the curvature of the transition between internal jugular and subclavian veins 92b, 92c.

In addition, as shown in FIG. 10B, the membrane 452 includes an aspiration port 458 therein, e.g., at an intermediate location between the ends 454 of the membrane 452, e.g., substantially centered in the outer surface 456 of the membrane 458. A lumen extension 470 extends from the aspiration port 458 and communicates with the aspiration lumen 416 of the catheter 410. For example, the lumen extension 470 may be an elastic or other flexible tube including a first end attached to the membrane 452 on an inner surface thereof (i.e., opposite the outer surface 456) around the aspiration port 458 and a second end attached to the distal end 414 of the catheter 410 adjacent the arms 462. Alternatively, the lumen extension 470 may be integrally formed with the membrane 452, e.g., molded or otherwise formed from a single piece of material.

In exemplary embodiments, the membrane 452 and/or lumen extension 470 may be formed from elastomeric material, e.g., silicone, and the like. In an exemplary embodiment, the membrane 452 and lumen extension 470 may be formed from a relatively low Durometer material compared to the distal end 414 of the catheter 410, e.g., to provide flexibility and/or conformance to the patient's anatomy, while the distal end 414 may translate forces via the frame 460 to engage the membrane around the ostium 94a of the thoracic duct 94, as described further below. In another embodiment, the lumen extension 470 may have a higher Durometer than the membrane 452 and/or may have a similar or lower Durometer than the distal end 414 of the catheter 410.

Turning to FIG. 11, during use, the apparatus 408 may be introduced into a patient's body, e.g., into the patient's venous system, to access and/or isolate the thoracic duct 94. In an exemplary procedure, an access site, e.g., percutaneous puncture or cut-down, may be created at a peripheral or other remote location in the patient's body (not shown), such as a femoral vein, a right or left internal jugular vein, or a right or left subclavian vein, and the distal end 414 of the catheter 410 may be introduced via the access site with the sealing member 450 in the delivery condition into the region 90, e.g., the confluence of the internal jugular vein 92b and the left subclavian vein 94c adjacent the thoracic duct 94.

For example, if the catheter 410 includes an instrument lumen, a guidewire or other rail (not shown) may be positioned from the access site into the confluence region 90, the guidewire may be backloaded into the instrument lumen, and then the catheter 410 may be advanced over the guidewire until the distal end 414 is positioned within or adjacent the confluence region 90. In addition or alternatively, a guide catheter (not shown) may be positioned from the access site into the confluence region 90 and the catheter 410 may be loaded into and advanced through the guide catheter (with or without a guidewire). In this embodiment, the frame 460 may be folded into the collapsed configuration to allow the sealing member 450 to be loaded into and advanced through the guide catheter in the delivery condition. Alternatively, the sealing member 450 may directed to the delivery condition using a sleeve on the catheter 410 or retracting the frame 460 at least partially into the distal end 414 of the catheter 410 before introduction, as described elsewhere herein.

Optionally, before the procedure, the thoracic duct 94 may be identified using external imaging, e.g., using external beam ultrasound, fluoroscopy, CT scanning, and the like. For example, the location and/or specific anatomic orientation of the thoracic duct 94 and adjacent anatomy may be identified and documented. This may involve creating a three-dimensional model, which may be displayed or otherwise presented to the medical personnel before or during the procedure. Alternatively one or more two-dimensional images may be acquired to facilitate preparation for the procedure. Such information may be used to determine the desired the venous approach used during the procedure, e.g., based on the location and/or orientation where outlet 94a of the thoracic duct 94 communicates with the central venous system.

For example, if the thoracic duct 94 enters where the left internal jugular vein 94b meets the subclavian vein 94c opposite the innominate vein 92a, a left or right femoral approach may be used, or the confluence region 90 may be accessed from the right internal jugular vein (not shown). The transverse orientation of the membrane 452 of the sealing member 450 may facilitate sealing of the ostium 94a using these approaches, as shown in FIG. 11 and described further below. Alternatively, a subclavian or internal jugular approach may be used, e.g., using the apparatus 708, 808 shown in FIGS. 15A, 15B, and 16, as described elsewhere herein.

Returning to FIG. 11, once the location and orientation of the thoracic duct 94 have been visualized, intermittent or continuous fluoroscopy may be used during the procedure, e.g., with contrast injection through an accessory lumen of the catheter 410, through a guide catheter, or other secondary instrument (not shown), to facilitate advancement and/or other positioning of the distal end 414 of the catheter 410. In addition or alternatively, external ultrasound may be used to monitor positioning of the distal end 414. In a further alternative, the catheter 410 may carry an ultrasound imaging element (not shown) on the distal end 414, which may be used to position and/or monitor the distal end 414 and/or sealing member 450 during the procedure.

Once the distal end 414 is positioned adjacent the outlet 94a of the thoracic duct 94, e.g., from the innominate vein 92a generally opposite the thoracic duct 94, the sealing member 450 may be deployed, e.g., be expanding the frame 460 to cause the membrane 452 to stretch and/or otherwise expand into the deployed condition. As shown in FIG. 11, once deployed, the outer surface 454 of the membrane 452 may be oriented away from the distal end 414 of the catheter 410, e.g., generally towards the outlet 94a of the thoracic duct 94.

In addition, the catheter 410 may be rotated and/or otherwise manipulated to align the arms 462 of the frame 460 in a desired orientation relative to the anatomy of the region 90, e.g., before or after deploying the sealing member 450. For example, as shown in FIG. 11, the first (substantially straight) arm 462a of the frame 460 may be oriented towards the internal jugular vein 92b and the second (generally "L" shaped) arm 462b of the frame 460 may be oriented towards the subclavian vein 92c, e.g., to align the outer surface 456 of the membrane 452 towards the outlet 94a. Optionally, one or both of the arms 462 may be malleable to modify the orientation of the arms 462 when deployed adjacent the thoracic duct 94, which may enhance engagement with the vessel wall adjacent the outlet 94a. In such an embodiment, the arms 462 may be plastically deformed into a desired orientation before the catheter 410 is introduced into the patient's body.

Once properly positioned, the catheter 410 may then be further advanced and/or manipulated to place the outer surface 456 of the membrane 452 against the vessel wall surrounding the outlet 94a, e.g., to substantially seal and/or isolate the thoracic duct 94 from the venous system. Distal force, e.g., torque or other forces, applied to the proximal end 412 of the catheter 410 may be transmitted to the distal end 414 to apply pressure against the vessel wall surrounding the outlet 94a, e.g., to enhance providing a substantially uniform and/or fluid-tight seal. Once the sealing member 450 is in place at the desired location, external ultrasound (and/or other imaging) may be used again to verify position and/or ensure that the thoracic duct 94 is substantially sealed.

Figure 12A:
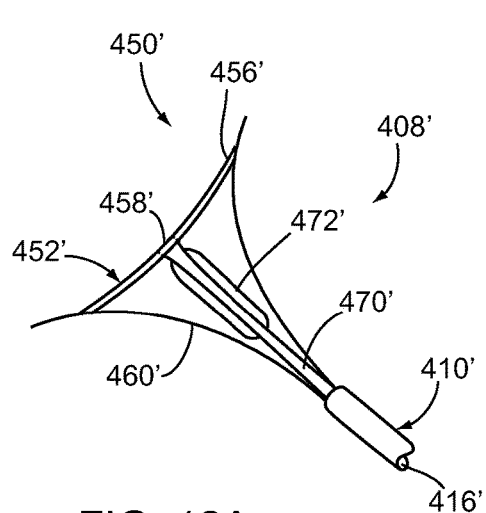
FIGS. 12A and 12B are side views of a distal portion of an alternative embodiment of the catheter shown in FIGS.
Figure 12B:
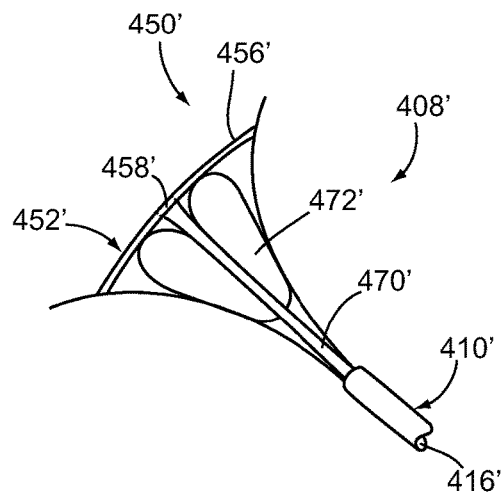

Optionally, the catheter 410 may include one or more features to enhance engagement and/or sealing of the membrane 452 around the outlet 94a. For example, as shown in FIGS. 12A and 12B, an alternative embodiment of a catheter 410' is shown that is generally similar to the catheter 410, e.g., including a sealing member 450' that includes a membrane 452' carried by an expandable frame 460' and a lumen extension 470' communicating between an aspiration port 458' in the membrane 452' and an aspiration lumen 416' in the catheter 410.'

However, in addition, the catheter 410' includes a balloon 472' on the extension lumen 470' immediately adjacent the inner surface of the membrane 452.' In this embodiment, the catheter 410' also includes an inflation lumen (not shown) extending from the proximal end of the catheter 410' and communicating with the interior of the balloon 472,' e.g., via a lumen in a wall of the lumen extension 470.' During use, the catheter 410' may be positioned within the confluence region 90 (not shown, see FIG. 11), the sealing member 450' deployed, and the membrane 452' placed against the vessel wall around the outlet 94a of the thoracic duct (also not shown). To enhance the seal, the balloon 472' may be inflated thereby applying a distal force against the inner surface of the membrane 452' to press the outer surface 456 of the membrane 452' further against the vessel wall around the outlet 94a.

Returning to FIG. 11, lymphatic fluid may then be aspirated or otherwise removed from the thoracic duct 94 via the outlet 94a, e.g., through the aspiration port 458 in the membrane 452, the lumen extension 470, and the aspiration lumen 416 of the catheter 410 to a location outside of the patient's body. For example, a container (not shown) may be coupled to the side port 422 of the handle 420 (shown in FIG. 10A), i.e., outside the patient's body, to collect the fluid, similar to other embodiments herein.

In one embodiment, the container may simply expose the path from the thoracic duct 94 to atmospheric pressure, which may provide sufficient pressure differential to remove fluid from the thoracic duct 94 at a desired flow rate, e.g., greater than eight hundred milliliters per hour (800 ml/hr). Optionally, a source of vacuum may be coupled to the container and/or the side port 422 on the handle 420 to increase the flow rate and/or otherwise enhance removal and collection of lymphatic fluid. The vacuum may also enhance engagement of the membrane 452 around the ostium 94a and ensure a fluid-tight seal, e.g., even if the distal force from the catheter 410 is reduced or removed.

In this manner, the apparatus 408 may be used to remove excess fluid via the thoracic duct 94 of a heart failure patient or otherwise remove lymphatic fluid completely from the patient's body. Optionally, the collected fluid may be used for other purposes, as described elsewhere herein. For example, the fluid may be separated in a desired manner, and a portion of the fluid reintroduced into the patient's body, similar to other embodiments herein.

Optionally, the apparatus 408 may include one or more sensors or safety elements, e.g., to identify fluid being removed using the catheter 410. For example, similar to other embodiments herein, a sensor in the container may identify the fluid being received therein, e.g., to confirm that the fluid is lymph and not whole blood. In one embodiment, an optical sensor may be provided at the inlet of the container (not shown) that may detect the color of fluid entering, e.g., to distinguish blood (which is red) and lymphatic fluid (which is generally clear to milky white). For example, if the sensor indicates that the fluid is not lymph, a valve may close to discontinue flow and/or receiving the fluid in the container and/or an indicator (e.g., a light or other visual indicator, a speaker or other audio indicator, and the like) may be activated, e.g., to inform medical personnel that the fluid is no longer just lymph. In another embodiment, the sensor(s) may detect one or more of pH of the fluid, perform pressure transduction, or perform chemical analysis (such as hematocrit, bicarbonate, or platelet count) of the fluid to identify the fluid or at least distinguish lymph from blood.

In an alternative embodiment, one or more sensors may be provided on the catheter 410, e.g., on the distal end 414 such that the sensor(s) are exposed to fluid entering the aspiration lumen 416 or on the handle 420 such that the sensor(s) analyze fluid leaving the catheter 410. In this alternative, the catheter 410 may include a switch, valve, or other actuator for closing the aspiration lumen 416 to discontinue flow of fluid and/or an indicator to inform medical personnel if the sensed fluid properties have changed. Thus, in this embodiment, the sensors may also provide an indication to the user whether the seal around the ostium 94a of the thoracic duct 94 has been compromised during the procedure, since the sensor(s) may quickly detect when fluid other than lymph is flowing through the catheter 410.

Once sufficient fluid has been removed, the sealing member 450 may be disengaged from the thoracic duct 94, returned to the delivery condition, e.g., by folding or otherwise collapsing the frame 460 and membrane 452, and the catheter 410 may be removed from the region 90 and the patient's body. If the catheter 410' of FIGS. 12A and 12B is used, the balloon 472' may be deflated before collapsing the frame 460 and membrane 452.

Turning to FIGS. 13A and 13B, another embodiment of an apparatus 508 is shown that includes a catheter 510 and a sealing member 550 generally similar to the embodiments described elsewhere herein. However, rather than a membrane, the sealing member 550 includes a resilient body 552 that is carried by a frame 560. In this embodiment, the resilient body 552 has sufficient structural integrity to be self-supporting unlike the membrane 452 of the catheter 410, e.g., such that the resilient body 552 is biased to a deployed condition, yet may be resiliently compressed into a delivery condition. For example, the resilient body 552 may formed from silicone or other elastomeric material, e.g., by molding, machining, and the like, to have a "C" shaped cross-section that extends in a curved shape between opposite ends 554, e.g., to define a concave outer surface 556, in a relaxed state, as shown in FIG. 13B.

The resilient body 552 may be attached to the frame 560 similar to other embodiments. For example, as shown, the frame 560 may include first and second arms 562, which are movable between a folded or collapsed configuration, e.g., as shown in FIG. 13A, and an expanded configuration, e.g., as shown in FIG. 13B. Similar to other embodiments herein, the arms 562 may include struts formed from elastic or superelastic material, which may bias the arms 562 to the expanded configuration, yet allow them to be resiliently folded into the collapsed configuration. Ends 554 of the resilient body 552 may be attached to respective arms 562, e.g., using similar methods and materials as other embodiments herein.

Similar to other embodiments, the sealing member 550 includes a flexible lumen extension 570 communicating between an aspiration port 558 in the outer surface 556 of the resilient body 552 and an aspiration lumen 516 in the catheter 510. The catheter 510 may include any of the optional features described with respect to other embodiments herein and/or may be included in a system, e.g., including a container for receiving lymphatic fluid, a source of vacuum, and the like (not shown).

During use, the catheter 510 may be introduced into a patient's vasculature with the sealing member 550 in the delivery condition shown in FIG. 13A, e.g., until the sealing member 550 is disposed adjacent the outlet 94a of the thoracic duct 94 (not shown, but generally similar to FIG. 11). The sealing member 550 may be deployed, e.g., by exposing and/or otherwise expanding the frame 560, whereupon the resilient body 552 may resiliently adopt the curved shape shown in FIG. 13B. The outer surface 556 of the resilient body 552 may be placed against the vessel wall surrounding the outlet 94a to substantially seal and/or isolate the thoracic duct 94, whereupon lymphatic fluid may be removed, e.g., collected in a container outside the patient's body, similar to other embodiments herein.

Turning to FIG. 14, yet another embodiment of an apparatus 608 is shown that generally includes a catheter 610 carrying a sealing member 650 similar to other embodiments herein. Unlike other embodiments, the sealing member 650 includes an annular ring 652 defining an aspiration port 658 and carried by a frame 660 that includes individual struts 668. Each strut 668 extends from the annular ring 652 into a lumen (which may be separate or the same lumen as the other struts) in the catheter 610, and is coupled to a respective actuator on a handle and/or proximal end (not shown) of the catheter 610. In the embodiment shown, the frame 660 includes four struts 668 coupled to the annular ring 652, and so four separate actuators may be provided on the catheter 610 such that each struts 668 may be advanced and/or retracted relative to the distal end 614 of the catheter 610. Alternatively, it will be appreciated that more or less individual struts may be included in the frame 660, as desired, e.g., based on the degree of control is desired for manipulating the annular ring 650.

For example, with all four struts 668 fully retracted, e.g., entirely into the catheter 610 or in close proximity to the distal end 614, the annular ring 652 may be folded or otherwise compressed inwardly into a delivery condition. The struts 668 may then be advanced individually or together to direct the annular ring 652 away from the distal end 614 of the catheter 610, e.g., to direct the annular ring 652 to the deployed condition. Once in the deployed condition, individual struts 668 may advanced and/or retracted, as desired, to change the shape of the annular ring 652, as described further below.

The annular ring 652 may be a flexible, resilient annular body that may be biased to the deployed condition yet may be resiliently compressed into the delivery condition. In an exemplary embodiment, the annular ring 652 may include a wire core 655, e.g., formed from elastic or superelastic material, similar to other embodiments herein, encased within or otherwise supporting a resilient body 653. The resilient body 653 may be formed from flexible and/or soft material, silicone or other elastomeric material, e.g., similar to the resilient body 552 of the catheter 510 described elsewhere herein.

For example, one or more wires may extend around the periphery of the annular ring 652 to define the wire core 655 and the struts 668 may be coupled to the wire(s), e.g., at locations spaced apart around the periphery. The wire core 655 and/or resilient body 653 may be biased to a desired shape, e.g., such that the resilient body defines an outer contact surface 656 that may have a concave shape and/or may be radiused similar to other embodiments herein for engaging the vessel wall surrounding the ostium of a thoracic duct (not shown). Alternatively, the wire core 655 and/or resilient body 653 may be relatively flexible without any bias or may be malleable such that the shape of the annular ring 652 may be adjusted.

For example, with the annular ring 652 in the deployed condition, individual struts 668 may be adjusted, e.g., to modify the shape of the entire annular ring 652 and/or the outer contact surface 656 (either elastically or without resistance from the wire core 655 and/or resilient body 653). In this manner, the shape of the outer contact surface 656 may be adjusted, e.g., based on the particular shape of the anatomy encountered, e.g., if the vessel wall surrounding the outlet of the thoracic duct varies substantially from a default shape, which may enhance the seal between the outer surface 656 and the vessel wall.

In an exemplary embodiment, the wire core 655 may be relatively flexible and/or elastic relative to the struts 668, e.g., such that the wire core 655 may be preferentially compressed rather than the struts 668 bending when the struts 668 are retracted into the catheter 610. For example, the wire core 655 may be formed from elastic or superelastic Nitinol, while the struts 668 may be formed from stainless steel.

Similar to other embodiments, the sealing member 650 also includes a lumen extension 670 extending between the aspiration port 658 of the annular ring 652 and an aspiration lumen (not shown) of the catheter 610. In this embodiment, the lumen extension 670 may have a tapered or other shape that sealingly engages the outer periphery of the resilient body 653 and transitions to direct fluid entering the aspiration port 658 into aspiration lumen. Alternatively, the annular ring 652 may include an inner wall (not shown) generally opposite the aspiration port 658 and the lumen extension 670 may be attached or otherwise coupled to the inner wall to substantially isolate the fluid path from the aspiration port 658 to the aspiration lumen.

The catheter 610 may be used generally similar to other embodiments herein. For example, the struts 668 may be actuated to compress the annular ring 652 into the delivery condition, and the distal end 614 of the catheter 610 may be introduced into the patient's body, e.g., into the confluence region 90 shown in FIG. 11. The struts 668 may then be advanced (individually or together) to deploy the annular ring 652, and, if desired, individual struts 668 may be adjusted to modify the shape of the deployed annular ring 652, e.g., before or after placing the outer contact surface 656 against the vessel wall surrounding the outlet 94a of the thoracic duct 94. Once a seal has been established, fluid may be removed from the thoracic duct 94, similar to other embodiments herein. After sufficient time or volume, the struts 668 may be retracted to compress the annular ring 652 back into the delivery condition, and the catheter 610 removed from the patient's body.

Turning to FIGS. 15A and 15B, still another embodiment of an apparatus 708 is shown for removing fluid and/or otherwise accessing a thoracic duct that includes a catheter 710 and a sealing member 750 constructed generally similar to the embodiments described elsewhere herein. For example, the catheter 710 generally includes a proximal end (not shown), a distal end 714 sized for introduction into a patient's vasculature, and one or more lumens, e.g., an aspiration lumen 716 extending between the proximal and distal ends 714.

The sealing member 750 generally includes a flexible membrane 752 attached to and/or carried by a frame 760 coupled to the distal end 714 of the catheter 710. The membrane 752 includes an aspiration port 758 communicating via a lumen extension 770 with the aspiration lumen 716 of the catheter 710, also generally similar to other embodiments herein. The frame 762 includes a pair of opposing arms 762 attached to ends 754 of the membrane 752, e.g., configured to stretch or expand the membrane 752 similar to other embodiments herein. The arms 762 may be biased to an expanded configuration yet may be resilient folded or otherwise compressed into a collapsed configuration, e.g., to allow the membrane 752 to be compressed into a delivery condition, also similar to other embodiments.

However, unlike previous embodiments, the frame 760 is shaped to accommodate a subclavian approach and deployment of the sealing member 750 within the confluence 90 of the internal jugular vein 92b and the left subclavian vein 92c. For example, instead of the arms 762 of the frame 760 being coupled to the catheter 7140, the arms 762 are coupled to a frame support 765, which is, in turn, attached to the distal end 714 of the catheter 710. The frame support 765 has a curved shape, e.g., such that the arms 762 and the membrane 752 are offset from a central longitudinal axis 718 on one side of the catheter 710. The frame support 765 may be biased to a predetermined shape and/or angle, e.g., an angle greater than ninety degrees (90°) relative to the longitudinal axis 718. Thus, the membrane 752 may be biased such that an outer surface 756 of the membrane 752 is oriented proximally partially towards the catheter 714 rather than distally away from the catheter 714 (e.g., as compared to the apparatus 410).

In addition, the catheter 710 includes a stabilization member 760 on an outer surface of the distal end 714, e.g., generally opposite the membrane 752. In the embodiment shown, the stabilization member 760 includes one or more mechanically actuated struts (one strut shown) that includes a first or proximal end 762 coupled to an actuator member 766 that extends to the proximal end of the catheter 710 and a second or distal end 764 fixed to the catheter 710, e.g., attached to an outer surface of the distal end 714. Thus, the stabilization member 760 may be movable between an inactive or low profile, e.g., as shown in FIG. 15A, and an active or expanded profile, e.g., as shown in FIG. 15B, upon actuation from the proximal end.

For example, a slider or other actuator control on a handle and/or the proximal end (not shown) of the catheter 714 may directed from a first position to a second position to advance the proximal end 762 of the stabilization member 760 towards the distal end 764, thereby causing the stabilization member 760 to bow or otherwise extend outwardly away from the catheter 710 generally opposite the membrane 752. In an exemplary embodiment, the stabilization member 760 may be formed from elastic or superelastic material, e.g., metals such as Nitinol, stainless, and the like, plastics, or composite materials, such that the stabilization member 760 may be directed back and forth between the inactive and active profiles.

In an alternative embodiment, shown in FIG. 16, a catheter 710' is shown generally similar to the catheter 710 except that a balloon 760' is provided on the distal end 714' opposite the membrane 752' of the sealing member 750.' An inflation lumen 716a' communicates with an interior of the balloon 760' for selectively expanding and collapsing the balloon 760' in a direction opposite the membrane 752.'

Returning to FIG. 15B, during use, the catheter 710 may be introduced into the patient's body with the sealing member 750 in a delivery condition. For example, the frame 760 may be folded or otherwise compressed into a collapsed configuration, e.g., by substantially straightening the frame support 765 and folding the arms 762, thereby collapsing the membrane 752. In an exemplary embodiment, the sealing member 750 may loaded into a guide catheter or other delivery sheath (not shown), which may constrain the frame 760 in the collapsed configuration, yet allow the sealing member 750 to be advanced through the delivery sheath previously positioned within the confluence region 90, similar to other embodiments herein. Alternatively, a sleeve (not shown) may be provided on the distal end 714 of the catheter 710 for constraining the sealing member 750, similar to other embodiments herein.

Once the distal end 714 of the catheter 710 and the sealing member 750 are positioned within the region 90, the sealing member 750 may be deployed, e.g., by advancing the sealing member 750 from the delivery sheath and/or retracting the delivery sheath. The frame 760 may be biased to the expanded configuration, thereby biasing the frame support 765 to the curved configuration and expanding the arms 762 to stretch or otherwise open the membrane 752, e.g., as shown in FIG. 15A. Optionally, additional manipulation may be used to allow the frame 760 to unfold into the expanded configuration, e.g., by advancing the sealing member 750 past the outlet 94a of the thoracic duct 94, e.g., into internal jugular vein 92b or other adjacent vein.

With the sealing member 750 in the deployed condition, the distal end 714 of the catheter 710 may be manipulated to orient the outer surface 756 of the membrane 752 towards the outlet 94a of the thoracic duct 94 and/or place the outer surface 756 against the vessel wall surrounding the outlet 94a. Because of the bias of the frame support 765 and/or the arms 762, the outer surface 756 may be pressed against the vessel wall sufficiently to substantially seal and/or isolate the thoracic duct 94 from the venous system.

To enhance and/or ensure an effective seal, the stabilization member 760 may then be deployed, e.g., causing the stabilization member 760 to bow or otherwise extend outwardly, e.g., until the stabilization member 760 contacts the vessel wall of the left subclavian vein 92c generally opposite the thoracic duct 94. Alternatively, if the balloon 760' of FIG. 16 is provided, the balloon 760' may be inflated to contact the vessel wall of the left subclavian vein 92c generally opposite the thoracic duct 94. In this manner, the stabilization member 760 (or 760') may apply additional normal force to press the outer surface 756 (or 756') of the membrane 752 (or 752') into a sealing engagement with the vessel wall surrounding the outlet 94a.

After the seal has been confirmed, fluid may be removed from the thoracic duct 94, e.g., through the aspiration port 758, lumen extension 770, aspiration lumen 716 of the catheter 710, and out of the patient's body, e.g., into a container, similar to other embodiments herein. Once sufficient fluid is removed, the stabilization member 760 may be returned to the low profile, the membrane 752 may be disengaged from the vessel wall, and the sealing member removed from the region 90 and the patient's body. For example, the catheter 710 may be retracted back into the delivery sheath to force the frame 760 to straighten and/or fold back into collapsed configuration, or a sleeve (not shown) may be advanced over the sealing member 750 to force the frame 760 to collapse. The catheter 710 may then be removed from the patient's body.

In alternative embodiments, other configurations may be provided for the sealing member instead of that shown in FIGS. 15A-16. For example, the sealing member may include a pair of struts (not shown) that extend distally from the distal end 714 of the catheter 710 and curve into a shape similar to the frame support 765. The struts may be spaced apart from one another and a membrane may be stretched or otherwise attached between the struts, e.g., at the curved portions of the struts. In this alternative, the struts may be substantially straightened, e.g., to provide a delivery condition, yet may be biased to the curved shape for placing the membrane against the vessel wall surrounding the outlet of the thoracic duct. Thus, in this embodiment, the sealing member may have a generally "J" or hook shape defining a concave contact surface for the membrane that may be directed against the vessel wall surrounding the outlet of the thoracic duct.

In addition or alternatively, one or more pullwires or other steering elements (not shown) may be coupled to the frame, e.g., to ends of the struts distally beyond the membrane. If desired, a proximal force may be applied to the steering element(s), e.g., to increase lateral and/or proximal forces applied between the membrane and the vessel wall surrounding the outlet of the thoracic duct.

It will also be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for accessing a thoracic duct of a patient's body, the thoracic duct including an outlet adjacent a confluence of an internal jugular vein and subclavian vein of the patient's body, comprising:
    a tubular member comprising a proximal end, a distal end sized for introduction into a patient's vasculature, and an aspiration lumen extending between the proximal and distal ends; and
    an expandable sealing member comprising:
        a frame comprising a first arm and a second arm movable between a collapsed configuration and an expanded configuration;
        a fluid-tight membrane comprising a first end coupled to the first arm and a second end coupled to the second arm such that the membrane is suspended between the first arm and the second arm free of additional supports, the membrane is expandable from a delivery condition sized for introduction into a patient's vasculature to a deployed condition in which the membrane defines a flexible concave outer contact surface extending between the first arm and the second arm and oriented away from the distal end, the outer contact surface configured to conform to a shape of a vessel wall surrounding the outlet of the thoracic duct for engaging a vessel wall surrounding the outlet of the thoracic duct to provide a fluid-tight seal isolating the thoracic duct from the internal jugular vein and the subclavian vein; and
        an aspiration port in the outer contact surface communicating with the aspiration lumen for removing fluid from the thoracic duct through the aspiration port into the aspiration lumen.

2. The apparatus of claim 1, wherein the membrane comprises opposing longitudinal edges extending between the first end and the second end of the membrane and defining a width of the membrane between the longitudinal edges, the membrane having a curved cross-section across the width in the deployed condition.

3. The apparatus of claim 2, wherein the membrane has a uniform width between the longitudinal edges along a length of the membrane between the first end and the second end.

4. The apparatus of claim 2, wherein an intermediate region of the membrane between the first end and the second end has an intermediate region width that extends between the longitudinal edges that is greater than an end width at the first end or the second end that extends between the longitudinal edges.

5. The apparatus of claim 1, wherein each of the first arm and the second arm includes first fixed ends coupled to the distal end of the tubular member and second free ends, and wherein the ends of the membrane are attached to the arms between the first fixed ends and the second free ends.

6. The apparatus of claim 1, wherein the first arm has an "L" or curved shape in the expanded configuration.

7. The apparatus of claim 6, wherein the second arm is substantially straight in the expanded configuration.

8. The apparatus of claim 1, wherein the first arm and the second arm are spaced asymmetrically relative to the distal end of the tubular member in the expanded configuration.

9. The apparatus of claim 1, further comprising a lumen extension extending between the membrane and the distal end of the tubular member and providing a fluid path between the aspiration port and the aspiration lumen.

10. The apparatus of claim 9, further comprising an expandable member on the lumen extension adjacent an inner surface of the membrane, the expandable member configured to expand and apply a distal force against the inner surface to press the outer contact surface against the vessel wall surrounding the outlet.

11. The apparatus of claim 1, wherein the membrane is oriented transversely relative to a longitudinal axis of the tubular member in the deployed condition.

12. An apparatus for accessing a thoracic duct of a patient's body, the thoracic duct including an outlet adjacent a confluence of an internal jugular vein and subclavian vein of the patient's body, comprising:
    a tubular member comprising a proximal end, a distal end sized for introduction into a patient's vasculature, a longitudinal axis extending between the proximal end and the distal end, and an aspiration lumen extending between the proximal and distal ends;
    a frame comprising first and second arms including first fixed ends coupled to the distal end of the tubular member and second free ends disposed distally beyond the distal end of the tubular member, the free ends movable away from one another to an expanded configuration in which the arms extend away from one another such that the free ends are spaced apart from one another and movable towards one another to a collapsed configuration; and
    a flexible sealing member comprising a flexible membrane including first and second ends attached to the first and second arms, respectively, such that the membrane is suspended between the first and second arms and defines an outer contact surface, the membrane movable between a delivery condition when the arms are in the collapsed configuration for introduction into a patient's vasculature and a deployed condition when the arms are in the expanded configuration in which the outer contact surface is oriented transversely relative to the longitudinal axis of the tubular member and shaped for engaging a vessel wall surrounding the outlet of the thoracic duct, the sealing member comprising an aspiration port in the outer contact surface communicating with the aspiration lumen for removing fluid from the thoracic duct through the aspiration port into the aspiration lumen.

13. The apparatus of claim 12, further comprising a flexible lumen extension extending between the aspiration port and the aspiration lumen.

14. The apparatus of claim 13, further comprising an expandable member on the lumen extension adjacent an inner surface of the membrane, the expandable member configured to expand and apply a distal force against the inner surface to press the outer contact surface against the vessel wall surrounding the outlet.

15. The apparatus of claim 12, wherein the first and second arms are spaced asymmetrically relative to a central longitudinal axis extending from the distal end of the tubular member in the expanded configuration.

16. The apparatus of claim 12, wherein the first arm has an "L" or curved shape in the expanded configuration.

17. The apparatus of claim 16, wherein the second arm is straight in the expanded configuration.

18. The apparatus of claim 12, wherein the arms are biased to the expanded configuration.

19. The apparatus of claim 12, wherein the membrane is attached to the frame only at the free ends of the first and second arms.

20. A method for accessing a thoracic duct of a patient's body, comprising:
- introducing a distal end of a tubular member into a patient's vasculature with a sealing member extending distally from the distal end in a delivery condition;
- advancing the tubular member until the distal end is disposed adjacent a junction of the patient's left internal jugular vein and the patient's left subclavian vein;
- deploying the sealing member adjacent the junction such that arms of a frame of the sealing member expand and a membrane suspended between the arms is expanded by the frame to extend transversely relative to a longitudinal axis of the tubular member and define a concave outer contact surface oriented away from the tubular member distal end;
- manipulating the tubular member to press the outer contact surface against a vessel wall surrounding an outlet of the thoracic duct, the outer contact surface conforming to a shape of the vessel wall to provide a fluid-tight seal isolating the thoracic duct from the left internal jugular vein and left subclavian vein; and
- removing fluid from the thoracic duct through an aspiration port in the outer contact surface communicating with an aspiration lumen within the tubular member.

* * * * *